(12) United States Patent
Barbot et al.

(10) Patent No.: US 11,278,303 B1
(45) Date of Patent: Mar. 22, 2022

(54) MINIMALLY INVASIVE SURGICAL DEVICES, SYSTEMS, AND METHODS

(71) Applicant: Vita Solutions LLC, Dunseith, ND (US)

(72) Inventors: Justin Barbot, Dunseith, ND (US); Jason Scherer, Woodbury, MN (US); Richard Arthur Thompson, St. Louis Park, MN (US); Thomas Arthur Tedham, Eden Prairie, MN (US); Reed Oliver Saunders, Minneapolis, MN (US)

(73) Assignee: Vita Solutions LLC, Dunseith, ND (US)

( * ) Notice: Subject to any disclaimer, the term of this patent is extended or adjusted under 35 U.S.C. 154(b) by 0 days.

(21) Appl. No.: 17/388,273

(22) Filed: Jul. 29, 2021

(51) Int. Cl.
*A61B 17/295* (2006.01)
*A61B 34/35* (2016.01)
*A61B 17/29* (2006.01)
*A61B 34/30* (2016.01)
*A61B 17/00* (2006.01)

(52) U.S. Cl.
CPC ........ *A61B 17/295* (2013.01); *A61B 17/2909* (2013.01); *A61B 34/35* (2016.02); *A61B 2017/00867* (2013.01); *A61B 2034/301* (2016.02); *A61B 2034/306* (2016.02); *A61B 2217/005* (2013.01)

(58) Field of Classification Search
CPC ... A61B 17/295; A61B 17/2909; A61B 34/35; A61B 2017/00867; A61B 2034/301; A61B 2034/306; A61B 2217/005
See application file for complete search history.

(56) References Cited

U.S. PATENT DOCUMENTS

| | | | |
|---|---|---|---|
| 7,087,071 B2 | 8/2006 | Nicholas et al. | |
| 8,504,201 B2 | 8/2013 | Moll et al. | |
| 9,017,371 B2 | 4/2015 | Whitman et al. | |
| 9,113,903 B2 | 8/2015 | Unger | |
| 10,307,199 B2 | 6/2019 | Farritor et al. | |
| 2008/0188868 A1 | 8/2008 | Weitzner et al. | |
| 2019/0183518 A1* | 6/2019 | Vidlund | A61B 17/22 |
| 2019/0282314 A1 | 9/2019 | Hegeman et al. | |

(Continued)

OTHER PUBLICATIONS

Amack et al., "Design and control of a compact modular robot for transbronchial lung biopsy," Medical Imaging 2019: Image-Guided Procedures, Robotic Interventions, and Modeling, Mar. 8, 2019, 10951:109510I, 8 pages.

(Continued)

*Primary Examiner* — Brooke Nicole Labranche
(74) *Attorney, Agent, or Firm* — Fish & Richardson P.C.

(57) ABSTRACT

A surgical instrument assembly is provided. In some embodiments, an example surgical instrument assembly includes a surgical instrument configured to pass through a guide tube having a proximal end and a distal end. The surgical instrument can include one or more arms configured to extend from the intermediate position, each arm having one or more joints positioned along the arm and an end effector attached at the distal end of each arm. The surgical instrument assembly can include a control assembly positioned at the proximal end and configured to control the movement of the joints and the end effectors.

32 Claims, 20 Drawing Sheets

(56) References Cited

U.S. PATENT DOCUMENTS

| | | |
|---|---|---|
| 2020/0000317 A1 | 1/2020 | Cooper et al. |
| 2020/0022562 A1 | 1/2020 | Milsom et al. |
| 2020/0107894 A1 | 4/2020 | Wallace et al. |
| 2020/0352666 A1 | 11/2020 | Danitz et al. |

OTHER PUBLICATIONS

Murgu, "Robotic assisted-bronchoscopy: technical tips and lessons learned from the initial experience with sampling peripheral lung lesions," BMC Pulmonary Medicine, Dec. 1, 2019, 19(1):89, 8 pages.

northhillsmonthly.com, "A New Weapon in the Fight Against Lung Cancer," NHM, Jul. 2020, 4 pages.

* cited by examiner

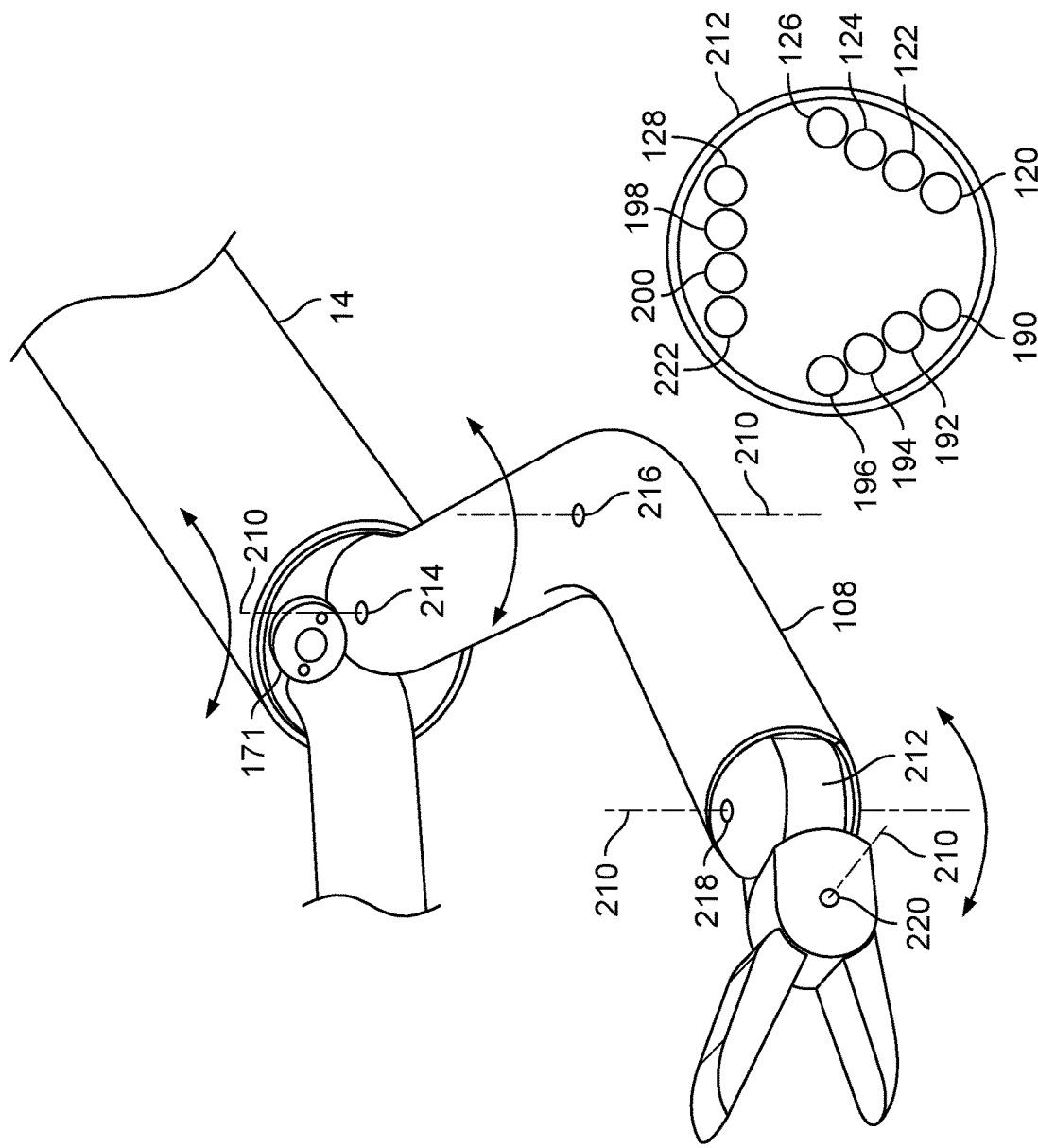

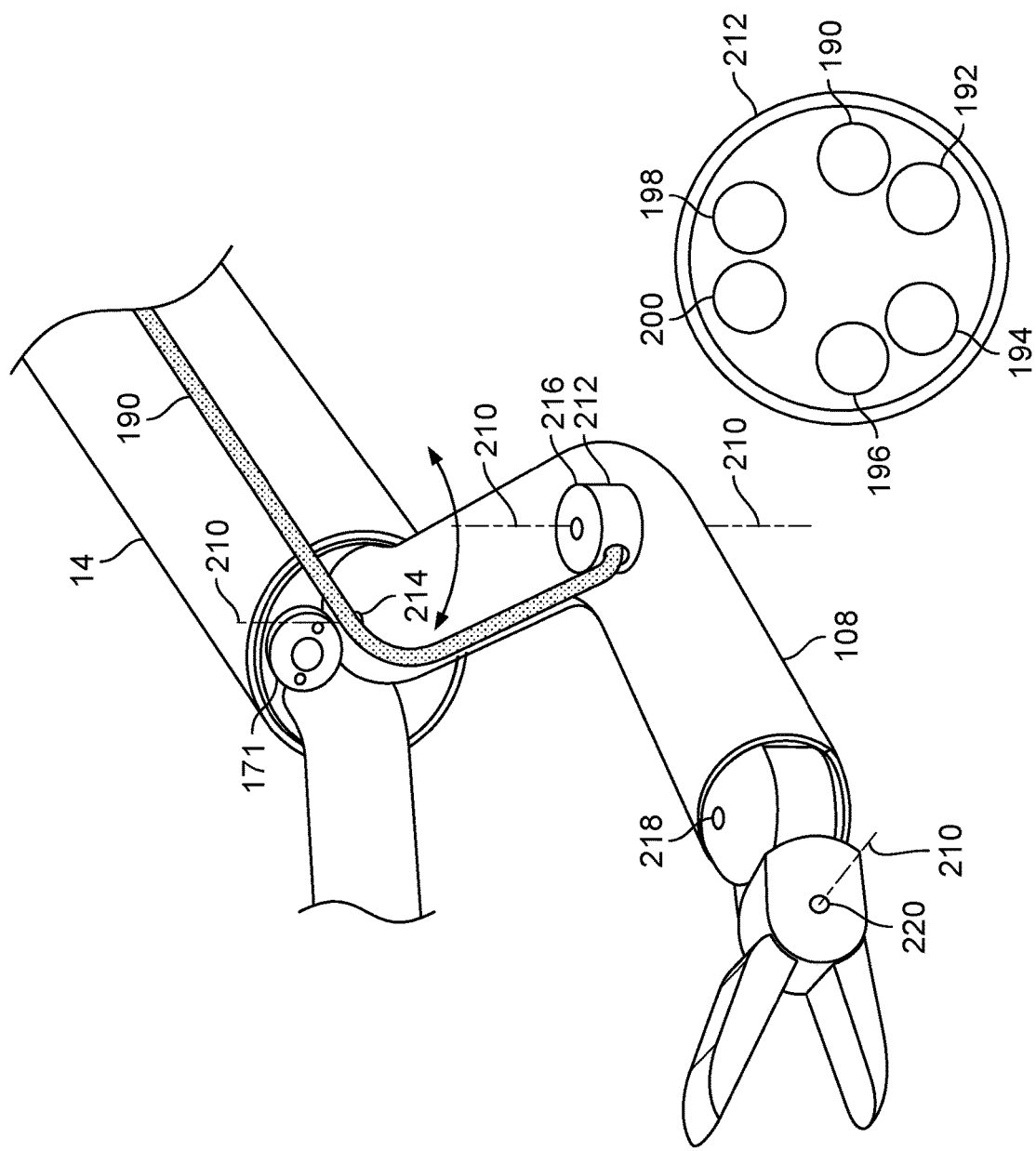

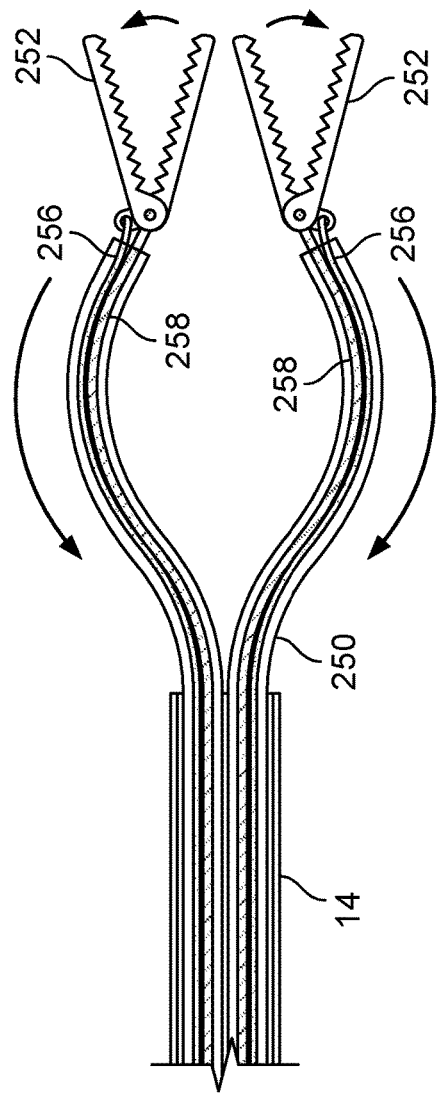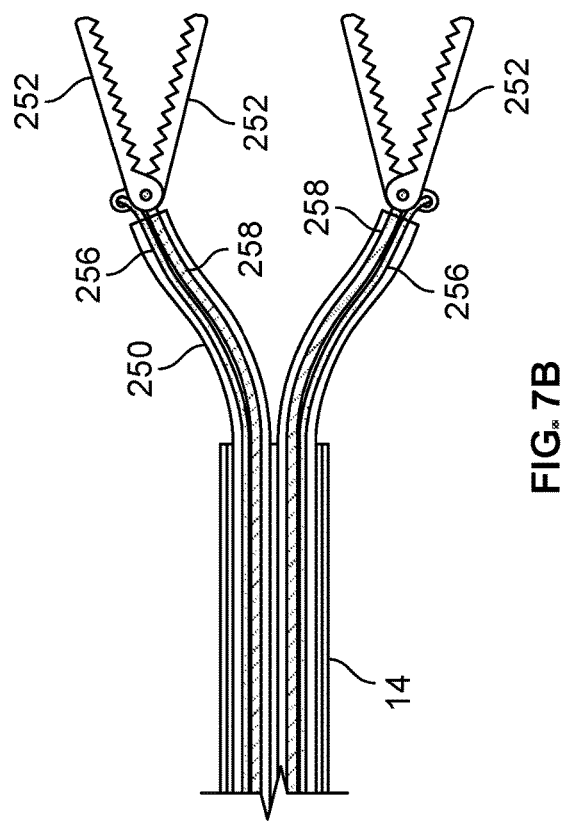
FIG. 7A
FIG. 7B

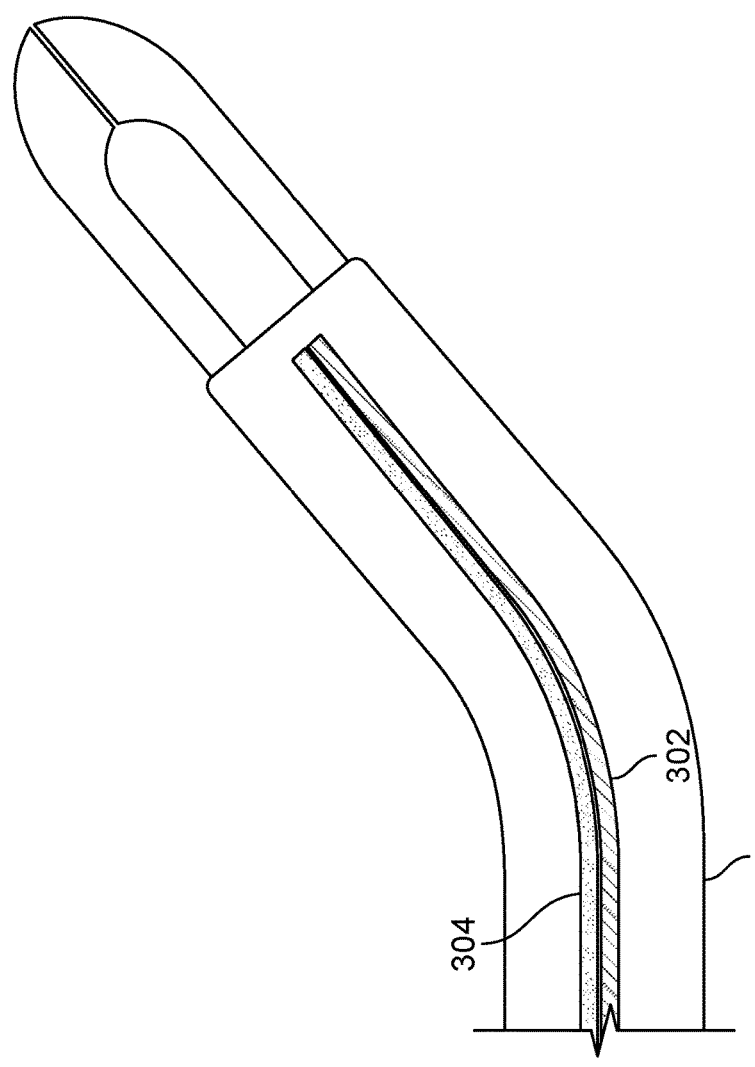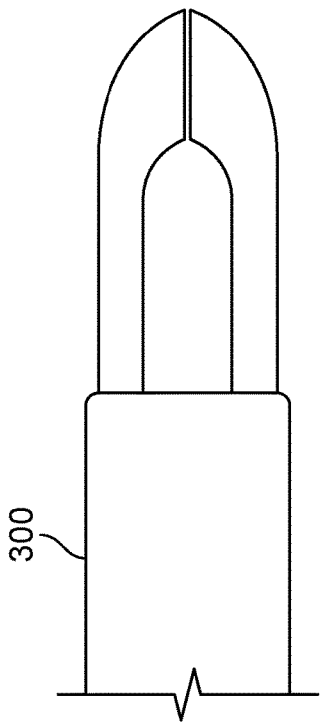

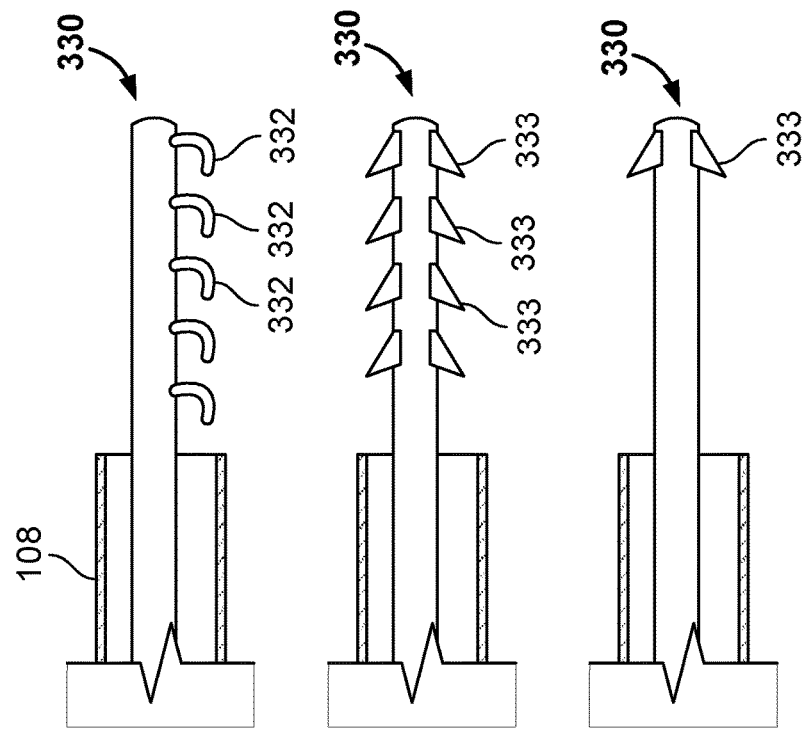
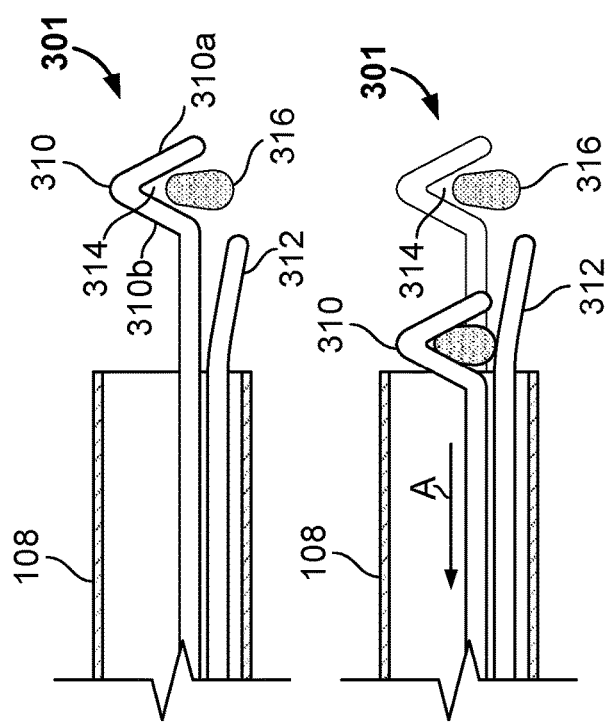
FIG. 10A
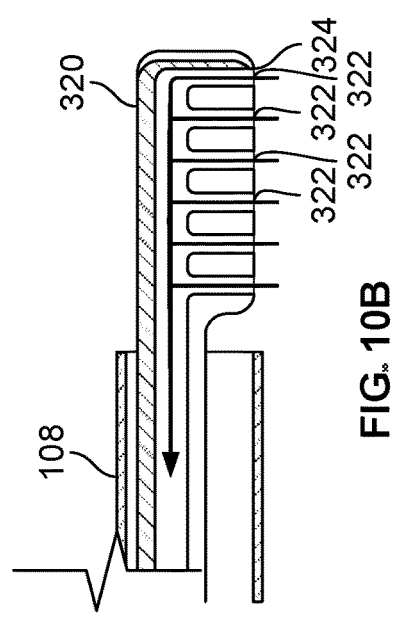
FIG. 10B
FIG. 10C

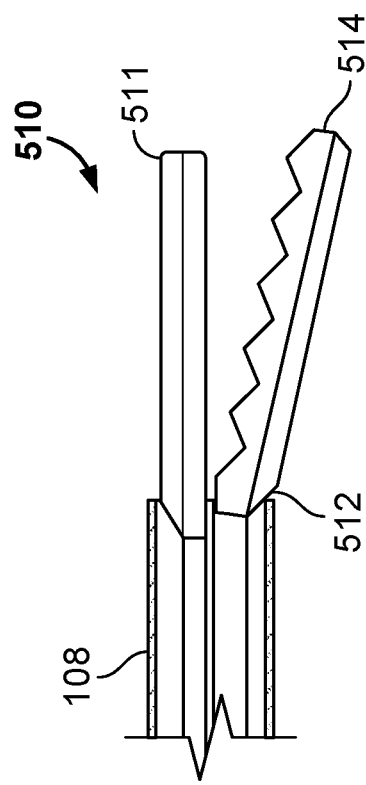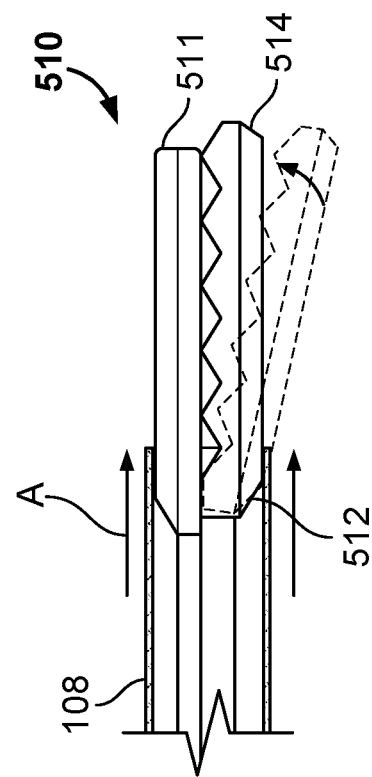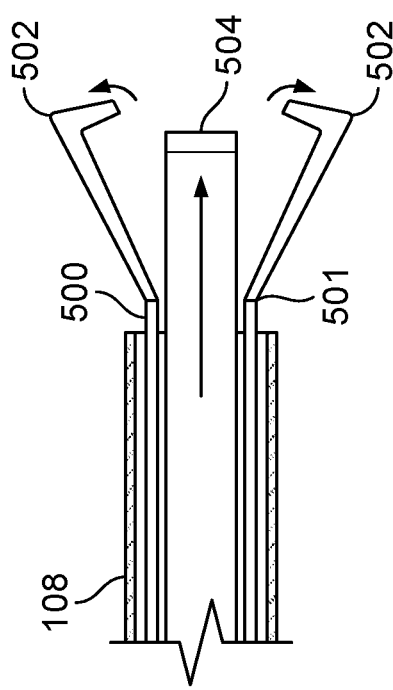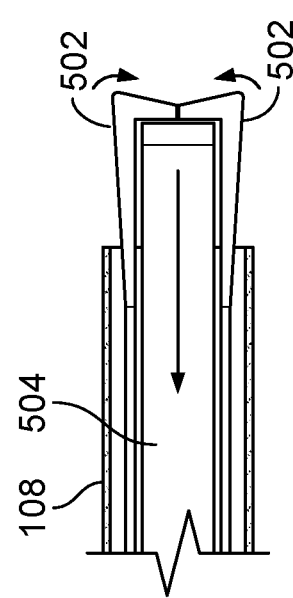
FIG. 12K
FIG. 12L
FIG. 12I
FIG. 12J

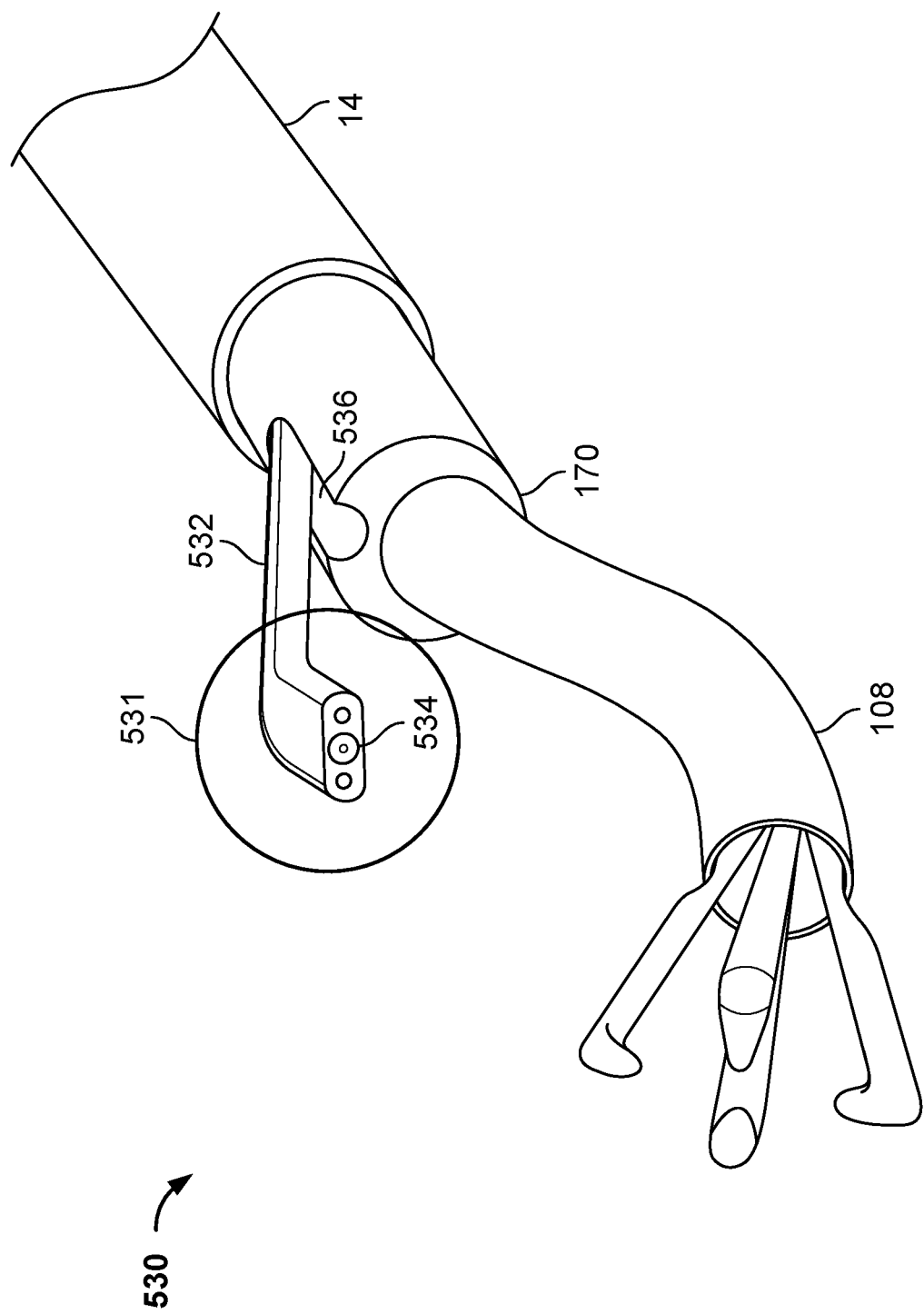

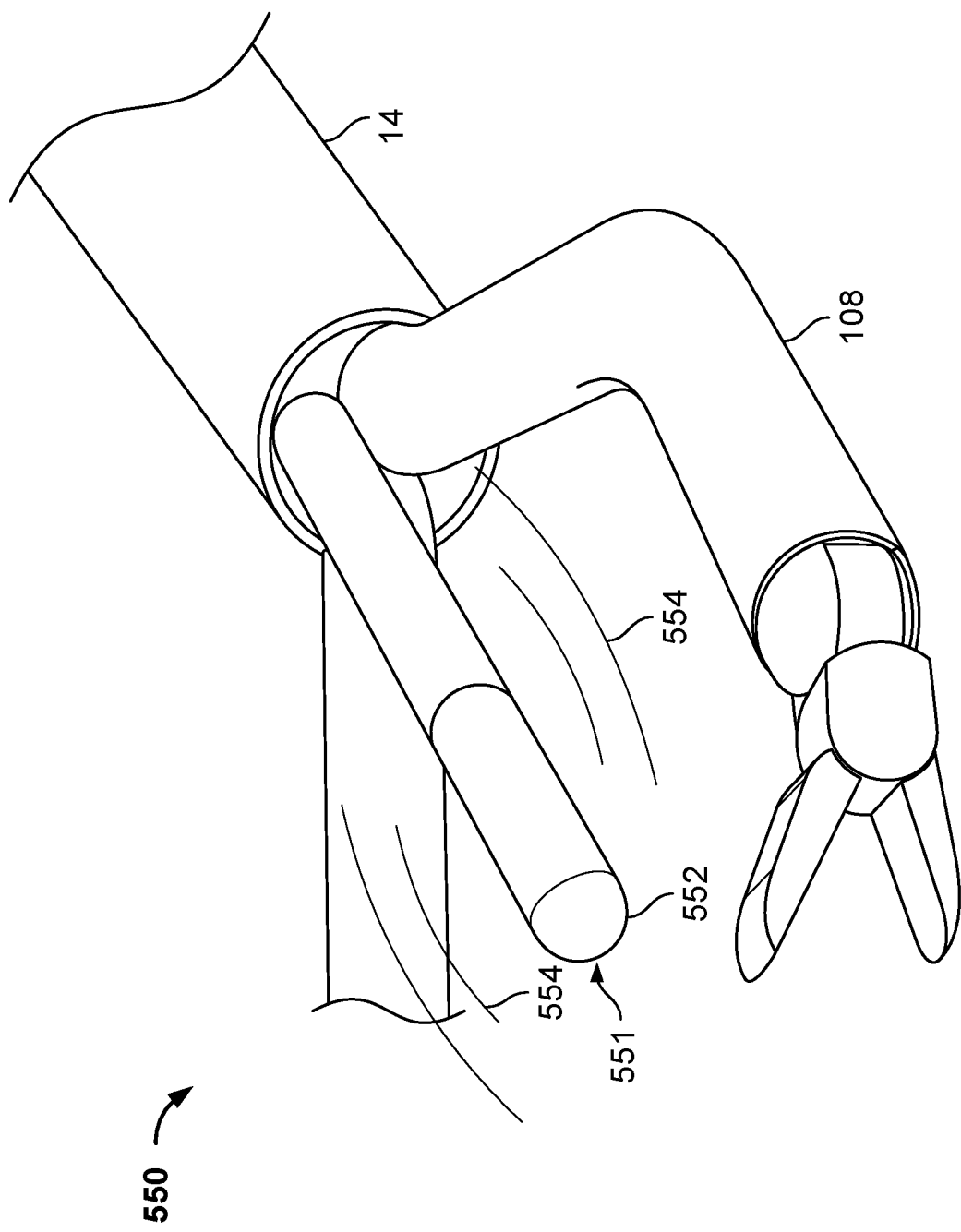

MINIMALLY INVASIVE SURGICAL DEVICES, SYSTEMS, AND METHODS

TECHNICAL FIELD

This document describes devices, systems, and methods related to minimally invasive surgical devices, for example, small-scale systems and devices used for minimally invasive surgery.

BACKGROUND

Minimally invasive surgery can include a variety of procedure types and approaches including endoscopy, laparoscopy, arthroscopy, endovascular, etc. Minimally invasive surgeries can include the use of both hand-held and teleoperated, telemanipulated, telepresence (robot assisted/telerobotics) equipment. Instruments can be inserted into a patient percutaneously via surgical incision or via natural orifice and are guided to a surgical site.

SUMMARY

Some embodiments described herein include devices, systems, and methods related to minimally invasive surgical devices configured to perform diagnostic and therapeutic surgical procedures. For example, a surgical instrument assembly includes a surgical instrument configured to pass through a guide tube. The surgical instrument optionally includes one or more arms each having one or more joints and an end effector attached to the end of each arm. Each arm may include one more joints that provide a number of degrees of freedom that uniquely identify the pose/configuration of the instrument assembly. The one or more arms are controlled by a control assembly positionable at a proximal end of the surgical instrument assembly. The control assembly is optionally connected to the one or more joints and end effectors via one or more components that translates the input at the control assembly to the output at the joints and end effectors.

In various example embodiments, the surgical instrument assembly facilitates manipulation of the arms and/or end effects via a small working channel (e.g., having a diameter of about 2 mm or less). For example, the arms and end effectors can be controlled with relatively fewer or no wires extending between the control assembly and the arms and/or end effectors. The arms and/or end effectors optionally include one or more memory shaped components that facilitate actuation by relative longitudinal or rotational adjustment between components of the arms, end effectors, and/or working channel. For example, a memory shaped component may be constrained by another component in a first position such that the end effector is in a first configuration, and when in a second position may move to a second configuration due to the bias of the memory shaped component.

In various example embodiments, the arms and end effectors are optionally manipulated by one or more a pressurized lumen, memory shaped component, biased hinge, rotational engagement, translational engagement, etc. In some embodiments, the arms and end effectors are manipulated without the use of a wire extending between the control assembly and arm joint/end effector.

The devices, systems, and methods described herein facilitate access to small anatomical positions that would otherwise be inaccessible by larger devices, systems, and methods. In addition to facilitating access to small anatomical positions, the devices, systems, and methods described herein also facilitate the articulation of surgical instruments in the small anatomical areas. The surgical instruments can include one or more arms, each arm can include an end effector, and the arms and end effectors can be controlled within the small anatomical environment to facilitate treatment within the area that otherwise would not be possible.

For example, surgical instrument assemblies described herein facilitate biopsy operations in relatively small anatomical locations in an atraumatic manner. Various surgical instrument assemblies optionally facilitate biopsy of tissue in the lung, such is for diagnosis and treatment of lung cancer and other illness.

In an example embodiment, a surgical instrument assembly includes a first arm having a proximal end and a distal end, a first end effector located at the distal end, a second arm having a proximal end and a distal end, a second end effector located at the distal end, and a control assembly located at the proximal ends of the first and second arms, the control assembly including a first end effector input that actuates the first end effector, a second end effector input that actuates the second end effector, a first arm input that controls at least one degree of freedom of the first arm, and a second arm input that controls at least one degree of freedom of the second arm. The first and second arms are configured to pass through a working channel having a diameter of 2 mm or less while the first and second arms and first and second end effectors are manipulated by the control assembly.

Various embodiments include some, all, or none of the following features. The control assembly includes a first control assembly housing and a second control assembly housing that is separate from the first control assembly housing, the first control assembly housing comprising a first handle, the first arm input, and the first end effector input, and the second control assembly housing comprising a second handle, the second arm input, and the second end effector input. Each of the first and second arms has a maximum outer diameter of less than 1 mm. The first arm does not include a wire extending between the proximal end and the end effector. Each arm includes a shoulder joint, an elbow joint spaced distally from the shoulder joint, a wrist joint spaced distally from the should joint and the elbow joint, and an effector joint spaced distally from the should, elbow, and wrist joints. The shoulder, elbow, wrist, elbow, and effector joints are controllable with a total of six wires or less within each arm. The assembly includes an imaging source that images an operating area that the arms and end effectors are configured to operate in. The shoulder joint, the elbow joint, the wrist joint, and the effector joint of the first arm are each independently controllable at the first control assembly. The surgical instrument is configured to extend through a working channel having a diameter of 2 mm or less. The end effector includes jaws for grasping and a blade for cutting. The first end effector comprises jaws adjustable between an open configuration and a grasping configuration. The first end effector is adjustable between the open configuration and the grasping configuration without manipulation of a wire connected with the first end effector. The first end effector is adjustable between the open configuration and grasping configuration by relative longitudinal movement between the first end effector and the first arm. The assembly includes a vacuum source in fluid communication with hollow channels of the end effector. The first arm comprises a memory shape such that the first arm exhibits a predefined curvature when extended from a working channel. The first arm comprises a memory shaped wire, the memory shaped wire having a curved profile in a rested state and a straight profile when electrified. The first arm comprises a pressurized lumen, a curvature of the arm adjustable by varying the pressure of the lumen.

In an example embodiment, a method of operating a surgical instrument assembly includes advancing first and second arms through a working channel having a diameter of 2 mm or less, the first arm having a proximal end and a distal end, a first end effector located at the distal end, and the second arm having a proximal end and a distal end, a second end effector located at the distal end, and manipulating a first control assembly located at the proximal end of the first arm to actuate the first end effector between an open configuration and a closed configuration while the first and second arms are located through the working channel, the first end effector actuated by movement of a portion of the end effector relative to the working channel.

In some embodiments, each of the first and second arms has a maximum outer diameter of less than 1 mm.

In some example embodiments, a surgical instrument assembly includes a first grasping means for grasping a target tissue, a first control means for actuating the first grasping means, and an arm extending between the first grasping means and the first control means.

The devices, system, and techniques described herein may provide one or more of the following advantages. First, some embodiments describe herein include a surgical instrument assembly that can access small anatomical positions while providing more than one arm having controllable articulation and controllable end effectors. For example, the one or more arms may be provided through a guide tube and/or working channel that is about, equal to, or below 2 millimeters (mm) in diameter. Surgical instrument assemblies described herein that can be delivered through guide tubes and/or working channels having such a size facilitate access to small anatomical areas, such as a lung, and/or reduce patient trauma and recovery. In some example embodiments, the surgical instrument assembly accesses a peripheral lung where the surgical instrument assembly may be utilized to perform minimally invasive lung biopsy.

Second, some embodiments described herein facilitate extending more than one working arm through a working channel having a diameter of about 2 mm or less. For example, two working arms may be inserted through and extend from a distal end of the working channel. In an example, each arm may have a diameter of 1 mm or less, while providing multiple degrees of movement that facilitate access and articulation of each arm within small anatomical areas.

Third, some embodiments described herein facilitate flexible and precise control of the orientation and positioning of the arms. For example, in some embodiments, each arm has an outer diameter of about 1 mm or less and each arm includes one or more joints or locations of articulation. For example, each arm may include two joints that facilitate articulation of each arm with multiple degrees of freedom. The surgical instrument assembly may provide two arms, each arm having a diameter of 1 mm or less, and each arm having two joints providing multiple degrees of freedom.

Fourth, some embodiments described herein facilitate manipulation of an anatomical structure by one or both arms. In an example embodiment, each arm includes an end effector positioned at a distal end of the arm. The end effectors facilitate grasping, cutting, imaging, and/or other end effectors. In some embodiments, the end effectors can work in conjunction with one another, such as by a first grasping end effector that can grasp an anatomical structure while a second cutting end effector can cut the anatomical structure (e.g., to treat, remove, biopsy, etc.). The end effectors can be manipulated in multiple degrees of freedom while having a diameter of less than 1 mm and/or extending at least partially through a working channel of about 2 mm or less.

Fifth, some embodiments described herein facilitate precise control and actuation of end effectors within a small anatomical location. For example, input at a control assembly (external to the patient) is translated to the end effector (within the patient) in a compact and reliable manner. In some embodiments, the input in translated without the use of a mechanical wire extending from the control assembly to the end effector. In various embodiments, translational, hydraulic, pneumatic, and/or electric techniques facilitate compact and robust operation of the end effectors.

The details of one or more implementations are set forth in the accompanying drawings and the description below. Other features and advantages will be apparent from the description and drawings, and from the claims.

DESCRIPTION OF DRAWINGS

FIG. 5A is a perspective view of an end of an example surgical instrument assembly.

FIG. 5B is a cross-sectional view of an exemplary joint of the surgical instrument assembly of FIG. 5A.

FIG. 6A is a perspective view of an end of another example surgical instrument assembly.

FIG. 6B is a cross-sectional view of an exemplary joint of the surgical instrument assembly of FIG. 6A.

FIG. 7A is a side view of an end of an example surgical instrument assembly having compliant arms and wire articulated jaws.

FIG. 7B is another side view of the surgical instrument assembly of FIG. 7A.

FIG. 9A is a side view of an end of an example surgical instrument assembly having spring metal to control the articulation of the arms.

FIG. 9B is another side view of the surgical instrument assembly of FIG. 9A.

FIGS. 10A to 10I illustrate various end views of embodiments of grasping end effectors of surgical instrument assemblies.

FIGS. 12A to 12L illustrate various end views of embodiments of grasping and/or cutting end effectors of surgical instrument assemblies.

FIG. 13 illustrates a perspective view of an end of a surgical instrument assembly having an imaging system.

FIG. 15 illustrates a perspective view of an end of a surgical instrument assembly having another imaging system.

DETAILED DESCRIPTION OF ILLUSTRATIVE EMBODIMENTS

Figure 1:
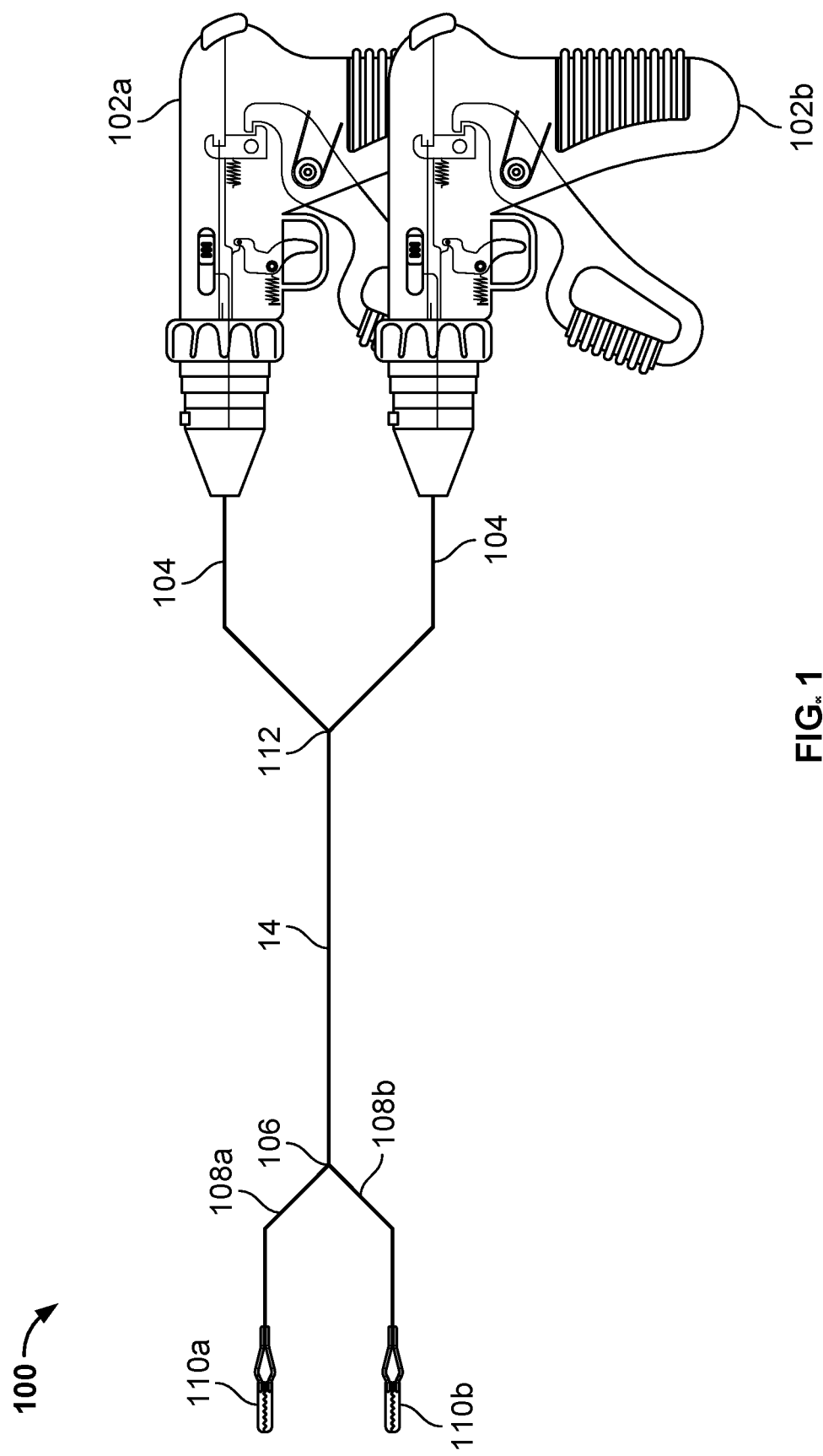
FIG. 1 is a side view of an example surgical instrument assembly.

Referring to FIG. 1, an example surgical instrument assembly 100 is shown that can be used in minimally invasive surgical and diagnostic operations. The surgical instrument assembly 100 includes one or more control assemblies 102 positioned at a proximal end of the surgical instrument assembly 100. During operation, the control assemblies 102a, 102b are positioned relative to a working channel 14 (e.g., of a surgical system) that extend into a patient. The surgical instrument assembly 100 includes one or more arms 108 that extend distally from the control assembly 102. The one or more arms 108 are positionable at least partially through the working channel 14 to access a target anatomical location. Each arm 108 (e.g. first and second arms 108) is connected to and controllable by the control assemblies 102, and each arm extends from the distal end of control assemblies 102 to one or more end effectors 110 positioned at the distal end of each arm 108. The one or more end effectors 110 are connected to and controllable by the control assemblies 102 via the arms 108 (e.g., which extend at least partially through the working channel 14). In an example embodiment, the working channel 14 terminates at an intermediate position 106 (e.g., within a patient), and the one or more arms 108 extend distally from the intermediate position 106.

The control assemblies 102 (e.g. control assemblies 102a, 102b) can be manipulated by a user to operate various effectors that control components of the surgical instrument assembly 100. In an example embodiment, surgical instrument assembly 100 includes a single control assembly 102. The single control assembly 102 is used to control one or more functions of one or more arms 108 and/or one or more end effectors 110. Alternatively or additionally, surgical instrument assembly 100 includes two or more control assemblies 102 that can be used to control components of the surgical instrument assembly 100. The control assemblies 102 control the articulation and movement of one or more of the arms 108 and the articulation, movement, and functionality of the end effector 110 connected to the distal end of the arm 108. For example, a first control assembly 102a controls one or more functions related to a first arm 108a and/or first end effector 110a, and a second control assembly 102b controls one or more functions related to a second arm 108b and/or second end effector 110b. Alternatively or additionally, each control assembly 102a, 102b is configured to control the articulation and movement of multiple arms 108 and the articulation, movement, and functionality of multiple end effectors 110 that are connected with each respective arm 108. In an example embodiment, surgical instrument assembly 100 includes a pair of arms 108a, 108b. In some embodiments, surgical instrument assembly 100 includes only a single arm 108, a pair of arms 108a, 108b, three arms 108, or more than three arms 108 that are at least partially manipulated via one or more control assemblies 102.

The control assemblies 102a, 102b can each include the same inputs. Alternatively or additionally, the control assemblies 102a, 102b include different effectors that facilitate different controls of various functions of the arms and end effectors (e.g., providing complementary functionality for a particular operation within the patient). For example, control assembly 102a includes effectors to control arm 108a and effector 110a. The effectors of control assembly 102a control the articulation of arm 108a and the grasping of effector 110a. Control assembly 102b includes effectors to control arm 108b and effector 110b, where the effectors of control assembly 102b control the articulation of arm 108b and the cutting of effector 110b. The effector of control assembly 102a that controls the articulation of arm 108a can be different than the effector of control assembly 102b that controls the articulation of arm 108b, where each effector at the respective control assemblies 102a, 102b are configured to provide degrees of freedom to each arm 108a, 108b. Similarly, the effector of control assembly 102a that controls the grasping of end effector 110a can be different than the effector of control assembly 102b that controls the cutting of end effector 110b.

The control assemblies 102 are connected to the arms 108 and end effectors 110, the arms 108 and effectors 110 are configured to at least partially extend through working channel 14. Each control assembly 102 is configured to control the arms 108 and end effectors 110 that extend through working channel 14, and each working channel 14 may remain independent of other working channels 14. For example, a working channel 14 may be positioned distally from each control assembly 102 and each working channel 14 may merge at an integration position 112 that allows the working channels 14 to combine and into a singular working channel 14. In another example, each working channel 14 does not include an integration position such that each working channel 14 extends independently of other working channels 14. Each working channel 14 may be connected to the control assembly 102 such that a proximal end of the working channel is maintained in a fixed position relative to the connection location of the control assembly 102. The working channel 14 is connected via a leur connection, a barbed connection, a threaded connection, a keyed connection, etc., such that the working channel 14 is connected and removable to and from the control assembly 102. The working channel 14 may be connected and disconnected from the control assembly 102, and the arms 108 and effectors 110 extend from the control assembly 102.

The arms 108 extend distally from the end of the working channel 14. Each arm 108 may include one or more joints that allow for the arm to be articulated in various directions at a position distal of the distal end of the working channel 14. Each arm 108 includes one or more end effectors 110 connected to a distal end of the arm 108. The end effectors 110 facilitate one or more grasping, cutting, or other functions, as described further herein.

Figure 2:
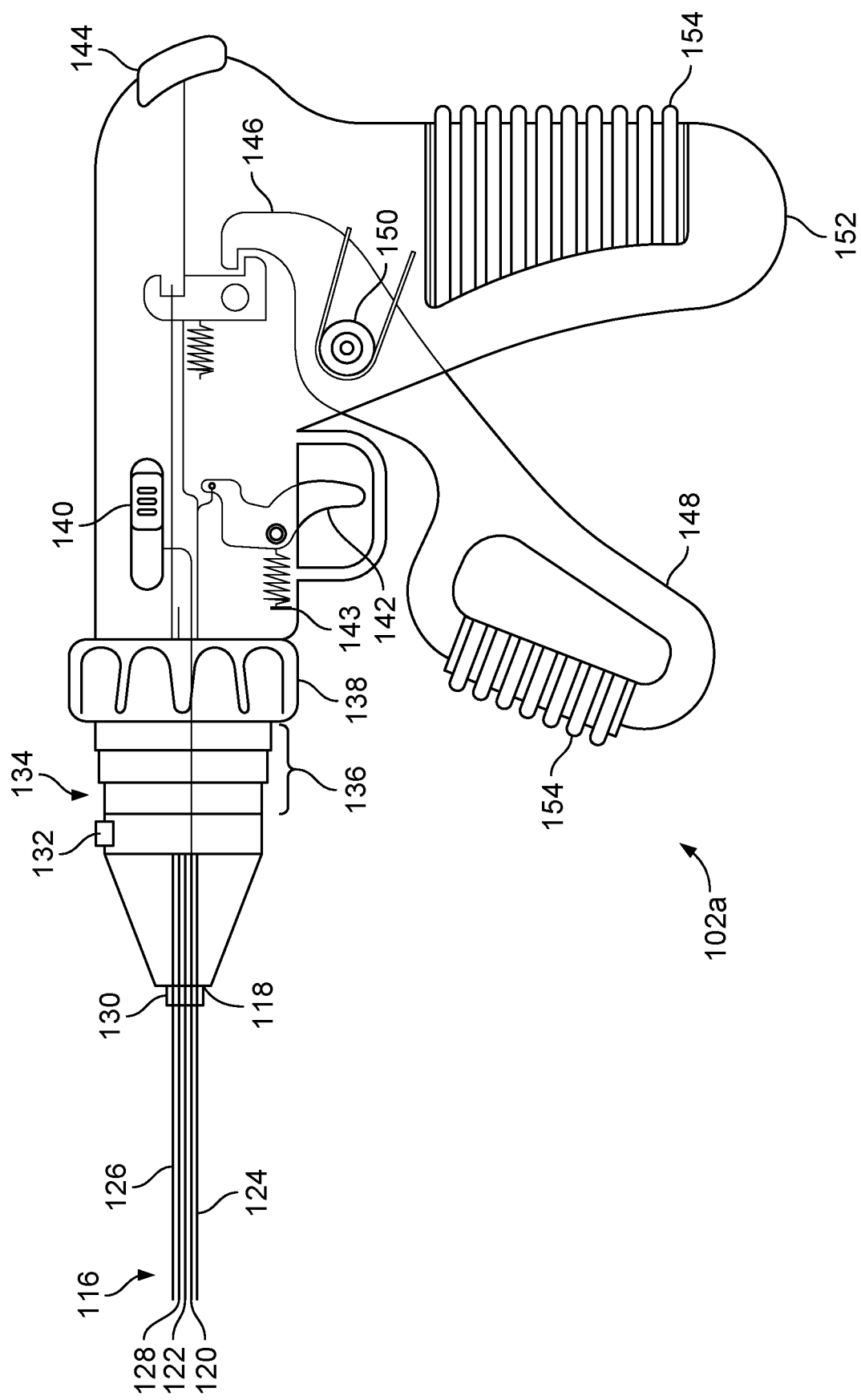
FIG. 2 is a side view of a control assembly of the surgical instrument assembly of FIG. 1.

FIG. 2 illustrates the first control assembly 102a. The control assembly 102a includes one or more user inputs that a user (e.g., healthcare practitioner) can manipulate to affect one or more functions of surgical instrument assembly 100. The control assembly 102 includes user inputs 136, 138, 140, 142, 146, and/or 144, to control various movements and functions of the arms and/or end effectors. For example, user inputs 136, 142, 146, and/or 144 can be manipulated to affect the longitudinal translation or extension, tilt, rotation, curvature, locking, and/or activation of arm 108 and/or end effector 110.

Surgical instrument assembly 100 includes one or more devices that translate manipulation of user inputs 136, 138, 140, 142, 146, and/or 144 into a corresponding response of arms 108, end effectors 110, and/or other portions of surgical instrument assembly 100. In an example embodiment, surgical instrument assembly 100 includes a plurality of mechanical wires 116 extending distally from a distal end 118 of the control assembly 102. The plurality of wires 116 extend into and are received by arm 108, and extend into connection with various components of the surgical instrument assembly 100 to affect one or more functions of the surgical instrument assembly 100. Alternatively or additionally, surgical instrument assembly 100 includes a plurality of pneumatic channels extending distally from a distal end 118 of the control assembly 102. The plurality of pneumatic channels may extend into connection with various components of the surgical instrument assembly 100 to affect one or more functions of the surgical instrument assembly 100. In another example embodiment, surgical instrument assembly 100 includes a plurality of hydraulic channels extending distally from a distal end 118 of the control assembly 102. The plurality of hydraulic channels extend into connection with various components of the surgical instrument assembly 100 to affect one or more functions of the surgical instrument assembly 100. In another example embodiment, surgical instrument assembly 100 includes any combination of one or more wires, one or more hydraulic channels, and one or more pneumatic channels, the combination of wires and channels providing a variety of control mechanisms for the arms and/or end effectors.

In some example embodiments, control assembly 102 is configured for remote operation by a user. The one or more devices that translate manipulation of user inputs 136, 138, 140, 142, 146, and/or 144 into a corresponding response of arms 108, end effectors 110, and/or other portions of surgical instrument assembly 100 are controlled by a wireless controller or other remote device that is physically separated (e.g., in a separate housing) and wirelessly connected to the surgical instrument assembly 100.

In an example embodiment, surgical instrument assembly 100 includes a plurality of mechanical wires 116. The plurality of wires 116 includes joint control wire 120 that connects the control assembly 102 to a joint of one of the arms 108. The joint control wire 120 facilitates control of the articulation and positioning of the joint. For example, retraction or tensioning (e.g. via input 140) of the wire 120 causes the joint to articulate, and extension or relaxation of the wire causes the joint to straighten, or vice versa.

The plurality of wires 116 include a catheter rotation wire 122 that facilitates control the rotational position of the working channel 14. For example, retraction, tensioning, or rotation of the catheter rotation wire 122 (e.g. via dial 138) causes the arm 108 to rotate in a first direction, and extension, relaxation, or opposing rotation causes the arm 108 to rotate in a second direction.

The plurality of wires 116 include a cutting action wire 124 that facilitates control the position and movement of an end effector (e.g. end effector 110) that includes a cutting mechanism. For example, retraction or tensioning (e.g. via trigger 142) of the wire 124 causes the cutting effector to retract within arm 108 and extension or relaxation of the wire causes the cutting effector to extend from the arm 108, or vice versa.

The plurality of wires 116 may also include a grasping wire 126 that controls an end effector (e.g. end effector 110) that includes grasping mechanisms which may also include cauterization. For example, retraction or tensioning (e.g. via lever 146) of the wire 126 causes the grasping effector to open and extension or relaxation of the wire 126 causes the grasping effector to close, or vice versa.

The plurality of wires 116 include a sensor wire 128 which may connect to an imaging source, a bronchoscope, a radial ultrasound probe, among other sensors that are implemented in surgical instrument assembly 100. For example, actuation, retraction or tensioning (e.g. via lever 146) of the wire 128 causes the sensor wire to turn on, causing the imaging source to begin imaging, bronchoscope to power on to begin imaging, and/or the ultrasound probe to turn on, among other sensor functions. Release, extension, or relaxation of the wire 126 causes the sensor sources to power off, or vice versa.

The control assembly 102 includes a connector 130 positioned at a distal tip of the control assembly 102 around the plurality of wires 116. The connector 130 is connected to and/or includes a connection to working channel 14 that is configured to receive the plurality of wires 116. The connector 130 retains the control assembly 102 in a fixed position relative to the working channel 14, the patient access opening, and/or target anatomical location where the end effectors operate. Precise manipulation can be translated from the control assembly 102 to the end effectors for accurate and precise operation (e.g., without the overall system including the control assembly 102 moving relative to the target location) when manipulated by the healthcare practitioner. For example, the connector 130 facilitates the telescopic spacer 136 to expand or retract by moving the handle portion 134 forwards and backwards while the connector 130 remains in a fixed position in relation to the working channel 14. In an example embodiment, the connector 130 is a luer lock that retains the control assembly 102 in a fixed position relative to working channel 14.

The control assembly 102 includes a telescopic spacer 136 that facilitates translation of a handle portion 134 in a longitudinal direction. The handle portion 134 is positioned between dial 138 and connector 130, and facilitates the longitudinal control of the arms 108 and/or end effectors 110. For example, the telescopic spacer 136 is extendible/compressible in a longitudinal direction (e.g., parallel with the direction that arms 108 extend from control assembly 102) such that the handle portion 134 is movable. Movement of the handle portion 134 via telescopic spacer 136 results in associated longitudinal movement of the arms 108 and/or end effectors 110 proximate the target anatomical location. The handle portion 134 is connected to the arms 108 and/or end effectors 110, and the connection between the handle portion 134 and the telescopic spacer 136 facilitates control of the longitudinal position of the arms 108 and/or end effectors 110. The telescopic spacer 136 can be connected to the arms 108 and end effectors 110 via one or more of the plurality of wires 116, via pneumatic channels, via hydraulic channels, combinations thereof, or any other suitable connection to facilitate control of the longitudinal position of the arms 108 and/or end effectors 110 via the telescopic spacer 136. The telescopic spacer 136 can thus facilitate intuitive control of arms 108 and/or end effectors 110 by manipulation of handle portion 134.

In an example embodiment, control assembly includes a handle lock 132 that locks the handle portion 134 of the control assembly 102 in a selected position. For example, the handle lock 132 prevents longitudinal movement of the handle portion 134 when engaged in a locked configuration. Alternatively or additionally, handle lock 132 prevents tilting movement (e.g., up and down or side to side) of the handle portion 134 when engage in a locked configuration. In some embodiments, the handle lock 132 prevents movement of handle portion 134 such that the arms 108 and/or end effector 110 is not manipulable via handle portion 134 when the handle lock 132 is engaged in the locked configuration, while the arm 108 and/or end effector 110 are manipulable by one or more other inputs of control assembly 102.

Control assembly 102 includes a dial 138 that controls the rotational position of arm 108. In an example embodiment, the dial 138 is connected to catheter rotation wire 122 and rotates (e.g., around handle portion 134 of control assembly 102) to manipulate the catheter rotation wire 122. Rotation of the dial 138 induces corresponding rotation of the arm 108 via the catheter rotation wire 122.

Control assembly 102 includes an input 140, such as a slider, that controls the articulation position of a joint. The slider 140 is connected to the joint control wire 120 and can actuate the joint control wire 120 to articulate the joint (e.g., in two directions). For example, manipulation of the slider in a first direction (e.g., distally) causes the arm 108 to pivot in a first pivot direction (e.g., to the left, and manipulation of the slider in a second direction (e.g., proximally) causes the arm 108 to straighten and/or pivot in a second pivot direction (e.g., to the right). Such manipulation can facilitate precise orientation of the end effector within the confines of a small target anatomical location via a relatively small working channel (e.g., about 2 mm or less). The slider 140 is lockable such that the position of the joint can be locked in place, and unlocked so that the joint can be repositioned.

A trigger 142 is connected to a cutting end effector via cutting action wire 124. The cutting action wire 124 controls the position and/or actuation of the cutting end effector. In an example embodiment, the trigger 142 is spring loaded via a spring 143 and is actuated in forward and backward directions to control the position of the cutting end effector. For example, the trigger 142 is placed in a first position (e.g., released) where the cutting end effector is retracted so that cutting does not occur, and the trigger 142 is placed in a second positon (e.g., squeezed/retracted) in which a sharp portion of the cutting end effector is exposed so that cutting may occur. Alternatively or additionally, the trigger may actuated to cause a cutting end effector to perform a cutting motion, such as by closing a cutting blade (e.g., in a scissor motion).

In some embodiments, control assembly 102 include a cauterization button 144 that causes the surgical instrument assembly 100 to heat/activate a cauterization end effector. The cauterization button 144 is lockable in an on position and/or lockable in an off position. Actuation of the cauterization button 144 causes a cauterization element (e.g. end effector having cauterization capabilities) to activate by heating/electrifying the element. Retraction of the cauterization button 144 causes the cauterization element to deactivate and cool.

A lever 146 controls the actuation of a grabbing end effector with extension and retraction of the lever 146, which can be pushed and pulled relative to handle 148. Lever 146 is connected to grasping wire 126 and can push and pull the grasping wire 126 to actuate jaws of a grasping end effector between open and closed positions. Lever 146 is spring loaded and controlled by handle 148. Handle 148 is lockable at various positions to facilitate grasping end effectors to grasp various sized items. The handle 148 is moveable via connection to joint 150 while grip 152 is stationary. Handle 148 and grip 152 may each include stabilizing grips 154 that improve the stability and grip for a user holding the handle 148 and grip 152.

Figure 3:
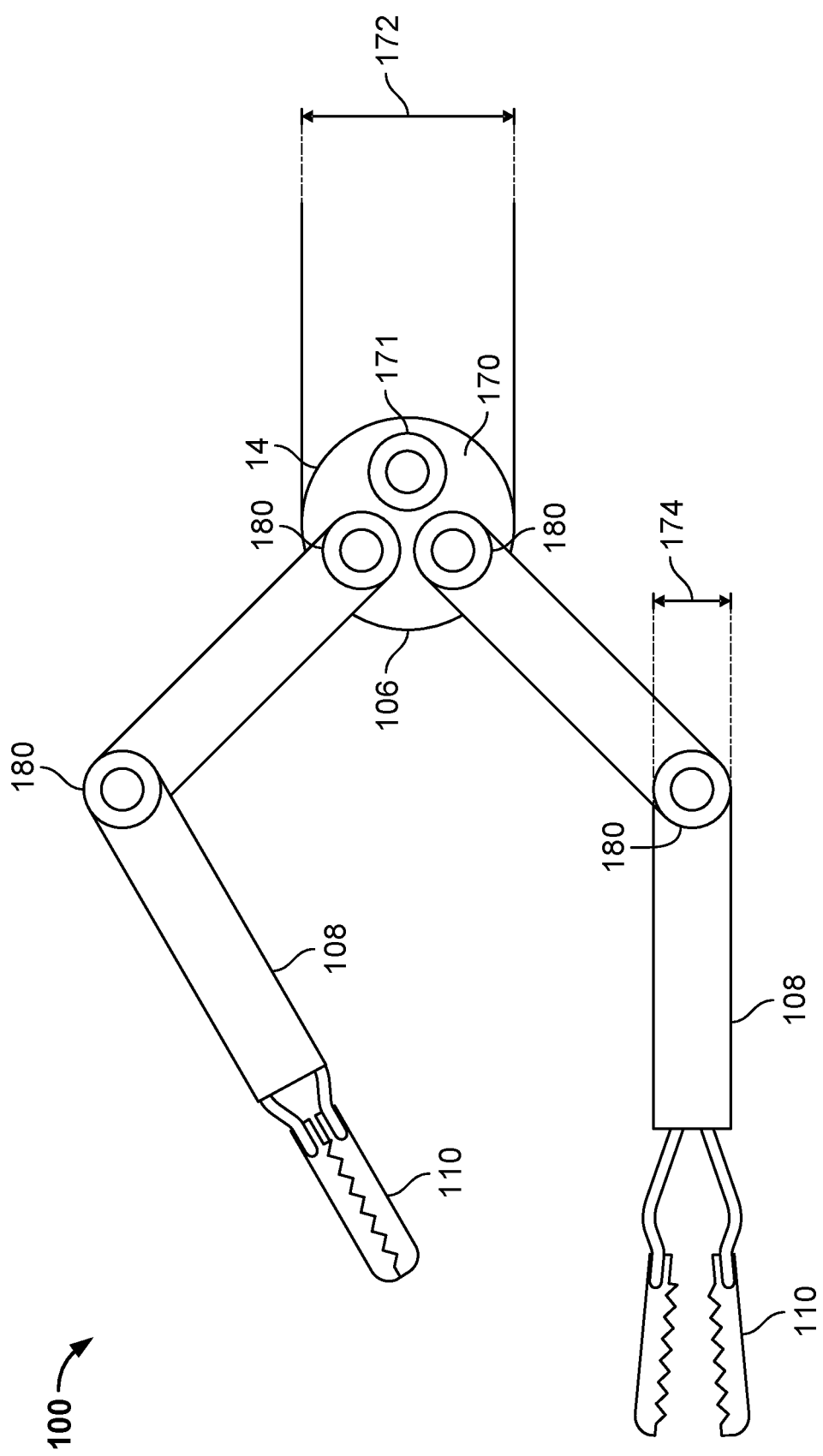
FIG. 3 is an end view of the surgical instrument assembly of FIG. 1, showing arms extending from the distal end of a working channel.
Figure 4:
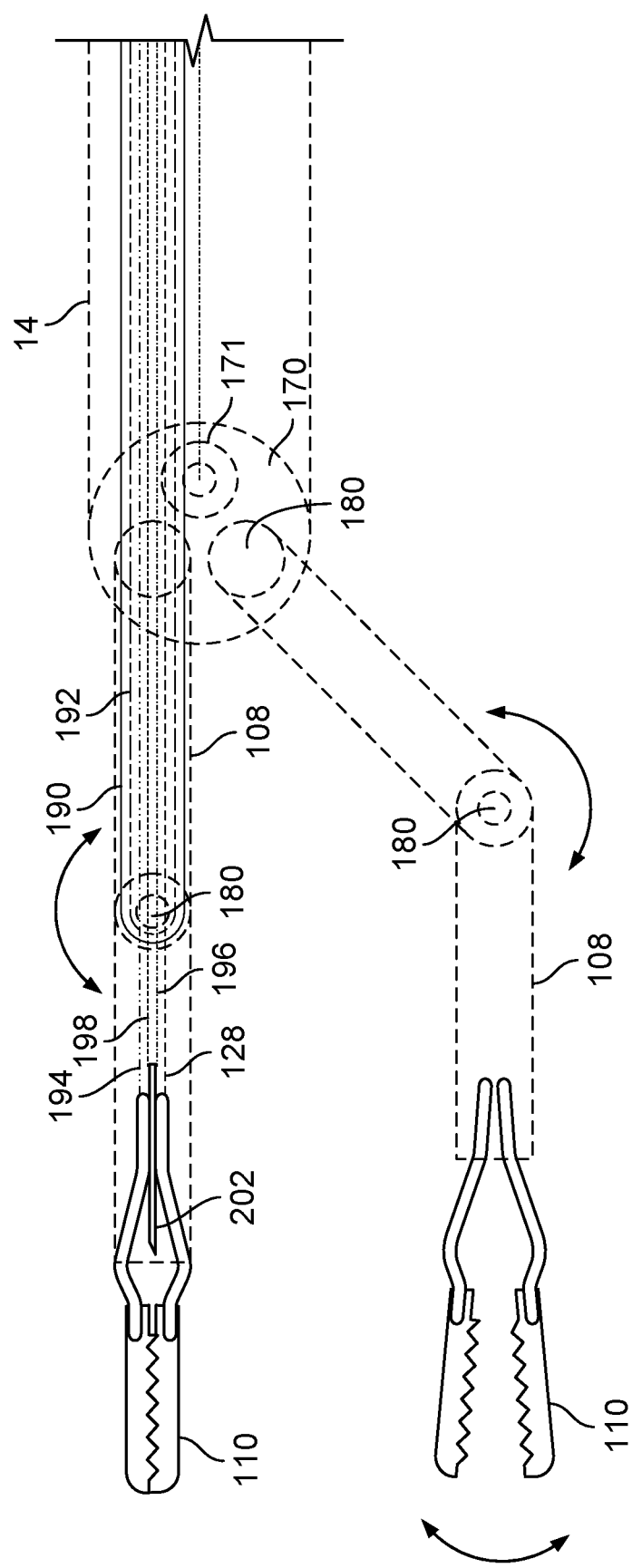
FIG. 4 is a partial sectional view of an end of the surgical instrument assembly of FIG. 1.

FIGS. 3 and 4 illustrate an end view of the surgical instrument assembly 100 including arms 108 that extend from a distal end 170 of working channel 14 during use. The distal end 170 of working channel 14 is at or near the same longitudinal position of the intermediate positon 106 shown in FIG. 1.

The distal end 170 is a distal face of the working channel 14 that includes one or more openings for each arm 108 and an imaging device 171. In various example embodiments, the working channel 14 has an outer diameter 172 between 1.0 mm and 8.0 mm, between 1.5 mm and 4.0 mm, between 1.75 and 2.5 mm, or a diameter 172 of about 2.0 mm.

Arms 108 may extend from the distal end 170 (e.g., within the outer diameter 172). In an example embodiment, the diameter 174 is the maximum dimension across the arm 108. In some embodiments, the diameter 174 of the arm 108 is a minimum space that the arm 108 can pass through within the working channel 14. The arms 108 have a substantially uniform diameter along the length of the arm 108. In some embodiments, the arms have a variable diameter along the length of the arm 108 in which the diameter reaches a minimum diameter (e.g. diameter 174) along a distal portion of the arm 108 that is configured to articulate within a target anatomical area. In an example embodiment, the arms 108 each have an arm diameter 174 of 1 mm. In various example embodiments, each arm 108 has an arm diameter 174 between 0.5 mm and 2.0 mm, between 1.0 mm and 1.25 mm, between 1.0 mm and 1.15 mm, or a diameter 174 of 1.0 mm. In an example embodiment, arms 108 have the same diameter (e.g. diameter 174). Alternatively, arms 108 have different diameters. For example, an arm 108 may have a larger diameter than one or more other arm 108s. The arms 108 having different diameters may facilitate positioning at least partially within, and extension from, a working channel having a defined sized (e.g., outer diameter 172), and may provide more space for a first arm 108 having particular functions that benefit from a large size as compared to a second arm 108 provided with a smaller arm diameter.

Arms 108 have one or more joints 180, each joint can be actuated and may rotate, pivot, or otherwise move to provide degrees of freedom of each arm 108. The degrees of freedom of each joint 180 are controlled by one or more of the plurality of wires 116 shown in FIGS. 2 and 4, and/or one or more other techniques described herein that provide manipulation corresponding to an input at the control assembly 102.

In an example embodiment, each joint 180 is independently controllable via control assembly 102. As shown in FIG. 4, the plurality of wires 116 extend from control assembly 102 through working channel 14 and arms 108 and include a swing out wire 190 that causes the joint 180 to swing outward such that the arm 108 moves away from a center line between the arms 108. The plurality of wires 116 can include a swing in wire 192 that may cause the joint 180 to swing inward such that the arm 108 moves towards a center line between the arms 108.

In some aspects, redundant manipulators have more than six joint degrees of freedom. Additional degrees of freedom can be used to control the function of the end effector. For example, in addition to the degrees of freedom controlling the position and orientation of the arms and end effectors, surgical instrument assembly 100 includes other degrees of freedom that control the function of the end effectors.

The plurality of wires 116 include an effector open wire 194 that may cause end effector 110 to open such that the jaws 195 of end effector 110 move away from each other in response to actuation of the effector open wire 194. The plurality of wires 116 include an effector close wire 196 that may cause end effector 110 to close such that the jaws 195 of end effector 110 move towards each other, which can include into contact with each other, in response to actuation of the effector close wire 196. In some example embodiments, surgical instrument assembly 100 facilitates adjustment of the jaws 195 using a single wire 194, alone or in conjunction with a spring or other biasing feature. The single wire 194 is controllable to draw the jaws 195 towards a first configuration, and controllable to allow the spring or other biasing feature to move the jaws 195 towards a second configuration.

The plurality of wires 116 include a blade extension wire 198 and a blade retraction wire 200, the blade extension wire 198 and the blade retraction wire 200 may control the longitudinal position of a surgical blade 202. For example. Actuation of the surgical extension wire 198 may cause the surgical blade 202 to move in a distal direction that moves outwardly away from the distal end of the arm 108, and actuation of the surgical retraction wire 200 may cause the blade 202 to move in a proximal direction that moves inwardly towards and into the distal end of the arm 108. The plurality of wires 116 include the sensor wire 128 described in reference to FIG. 2 above.

FIG. 5A illustrates a partial perspective view of a distal portion of the surgical instrument assembly 100 having arms 108 extending from the distal end 170 of the working channel 14, and illustrates arms 108 having multiple joints. For example, each arm 108 includes four joints, including a shoulder joint 214 positioned nearest to the distal end 170 of working channel 14, an elbow joint 216 positioned distally apart from the shoulder joint 214 and proximal to a wrist joint 218, the wrist joint 218 positioned distally apart from the elbow joint 216 and proximal to an effector joint 220. Accordingly, the four joints are positioned along the length of the arm 108 to provide degrees of freedom at different positions of the arm 108. Each joint may define a joint axis 210 about which the joint rotates, and each joint axis 210 may extend through a center of each joint. In some aspects, each joint may include a disc 212 that one or more wires can connect to (e.g. one or more of the plurality of wires 116) that can rotate about the joint axis 210 that extends through a face of the disc 212.

The orientation of each joint may determine the orientation of the joint axis 210 about which the joint 180 can rotate. For example, shoulder joint 214, the elbow joint 216, and the wrist joint 218 are aligned such that each joint axis 210 is oriented in the same direction, while the effector joint 220 is rotated such that the orientation of the effector joint 220 is at or near 180 degrees offset from the orientation of the wrist joint 218. Each of the shoulder joint 214, elbow joint 216, wrist joint 218, and effector joint 220 are independently controlled, providing the surgical instrument assembly 100 with the ability to manipulate arms 108 as needed.

In the exemplary aspects shown in FIGS. 5A and 5B, each joint can include connections to twelve (12) wires that allow for control of the articulation of the arms 108 and the end effector(s). The wires connected to each joint can include any of the plurality of wires 116 described above, including joint control wire 120, catheter rotation wire 122, cutting action wire 124, grasping wire 126, sensor wire 128, swing out wire 190, swing in wire 192, effector open wire 194, effector close wire 196, blade extension wire 198, blade contraction wire 200, a cauterization wire 222 and any combination thereof. The plurality of wires 116 are utilized in wire-and-pulley mechanics to provide for a miniaturization of the kinematic chain that controls the surgical instrument assembly 100. In an example embodiment, each of the wires extends along at least a portion of the length of the arm 108, and are arranged in three groups of four wires in a triangular pattern (e.g., as shown in FIG. 5B).

FIGS. 6A and 6B illustrate an exemplary embodiment of the surgical instrument assembly 100 in which each arm 108 includes connections to six (6) wires that facilitate control of the articulation of the arms 108 and the end effector(s). In some examples, a reduction in the number of wires connected to each joint may provide for wires having larger diameters than the examples including twelve wires for a given arm diameter. Larger diameter wires may provide an increase in strength of the joints and arms 108, and a related increase in robust actuation of the joints and arms (e.g., such that the wires can be subjected to relatively higher forces during operation). Relatedly, relatively fewer wires can facilitate a relatively smaller arm diameter such that the arm can pass through a relatively smaller working channel. In some embodiments, such a configuration can facilitate less invasive and atraumatic operation and/or access to relatively smaller target anatomical locations.

Referring to FIG. 6A, elbow joint 216 includes a wire (e.g. swing out wire 190) and a disc 212. The swing out wire 190 engages with the disc 212 (such as by insertion in an aperture into a circumferential face of the disc 212 or otherwise connecting with disc 212) to control the rotational position of the disc 212. Joint 212 is sprung in one direction with one of the plurality of wires 116 actuating in the opposite direction. For example, the disc 212 is biased by a spring in a first direction, and the wire 190 can be manipulated to act in the opposite direction. Loosening the wire can induce motion in the first direction (e.g., due to the spring bias) and tensioning the wire can induce motion in the second direction (e.g., by overcoming the spring bias). Such a configuration can facilitate control of motion in multiple directions at each joint while utilizing a single wire between the joint and control assembly. In an example embodiment, only a single wire extends between the control assembly and each of the shoulder joint 214, elbow joint 216, wrist joint 218, and effector joint 220. Alternatively or additionally, one or more of the single wires are actuated in only a single direction, with the spring bias acting to move the joint in an opposite, second direction. In some embodiments, the surgical instrument assembly 100 includes two arms 108, with two or more wires (e.g., joint control wire 120, catheter rotation wire 122, cutting action wire 124, grasping wire 126, sensor wire 128, swing out wire 190, swing in wire 192, effector open wire 194, effector close wire 196, blade extension wire 198, blade contraction wire 200, a cauterization wire 222) extending through the arm and actuated only in a single direction to control operation of a respective joint or component.

The wires connected to each joint can include any of the plurality of wires 116 described above, including joint control wire 120, catheter rotation wire 122, cutting action wire 124, grasping wire 126, sensor wire 128, swing out wire 190, swing in wire 192, effector open wire 194, effector close wire 196, blade extension wire 198, blade contraction wire 200, a cauterization wire 222 and any combination thereof. The plurality of wires 116 are utilized in wire-and-pulley mechanics to provide for a miniaturization of the kinematic chain that controls the surgical instrument assembly 100.

In various example embodiments, surgical instrument assembly 100 includes one or more techniques to facilitate arm control, alternatively or additionally to mechanical wire controlled joints (e.g., having one or more features described above). Referring now to FIGS. 7A and 7B an example surgical instrument assembly is shown that includes compliant arms 250 and end effectors 252 (e.g., articulated jaws). The compliant arms 250 include a memory shaped material (e.g., memory shaped wire/conduit) that facilitate arm positioning and control of the orientation of the jaws 252 while maintaining a compact outer profile of the compliant arms 250 that can fit within a relatively small working channel (e.g. working channel 14 having a diameter of about 2 mm or less). Compliant arms 250 are collapsible such that the arms 250 can retract into the working channel 14 when not in use and can extend outwardly from the working channel 14 when in use.

The relative positioning of distal ends of arms 250 and jaws 252 are manipulable by extension and retraction. As the distal ends of one or both arms 250 are extended from the working channel 14, the distal ends of the arms 250 are released from working channel 14 and at least partially unconstrained to form the memory shaped profile. In an example embodiment, the arms 250 have a curved shape or bowed shape such that the jaws 252 extend towards each other (e.g., as illustrated in FIG. 7A). The relative positioning of the ends of arms 250 and jaws 252 can be manipulated by adjusting a distance the arms 250 are extended or retracted (e.g., relative to the distal end of the working channel 14). In an example embodiment, the arms 250 and/or jaws 252 extend outwardly away from one another when the arms 250 are partially contracted (e.g., as illustrated in FIG. 7B) and form an elliptical or curved shape such that the arms 250 and jaws 252 are nearly contacting one another when the arms 250 are extended a maximum distance (e.g., relative to the distal end of the working channel 14).

In an example embodiment, jaws 252 are connected to upper jaw wire 256 and lower jaw wire 258 that extend through working channel 14 to control assembly 102. A healthcare practitioner can manipulate the control assembly 102 to operate jaws 252 via the upper jaw wire and/or lower jaw wire. Alternatively or additionally, jaw 252 is actuated using one or more techniques described herein, such as utilizing a single wire and/or spring-biased feature, a pressurized lumen, wireless (e.g., remote control) actuation, etc.

The memory-shaped compliant arms 250 facilitate positioning in a variety of locations and orientations (e.g., with the orientation of the jaw 252 selectable based on the positioning of distal ends of the arms 250), with relatively few moving parts and a compact overall volume.

Figure 8A:
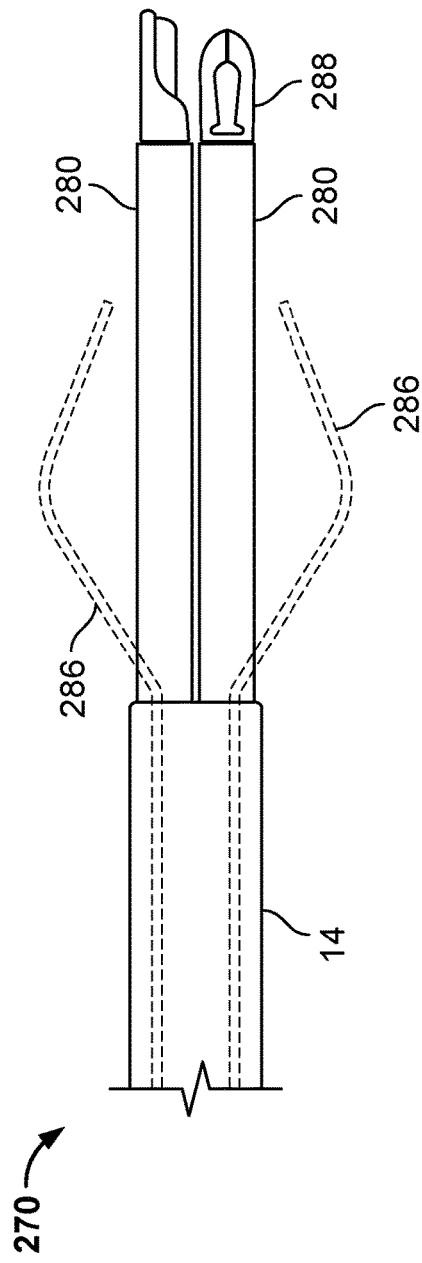
FIG. 8A is a side view of an end of an example surgical instrument assembly having spring metal and an inflatable channel to control the articulation of the arms.
Figure 8B:
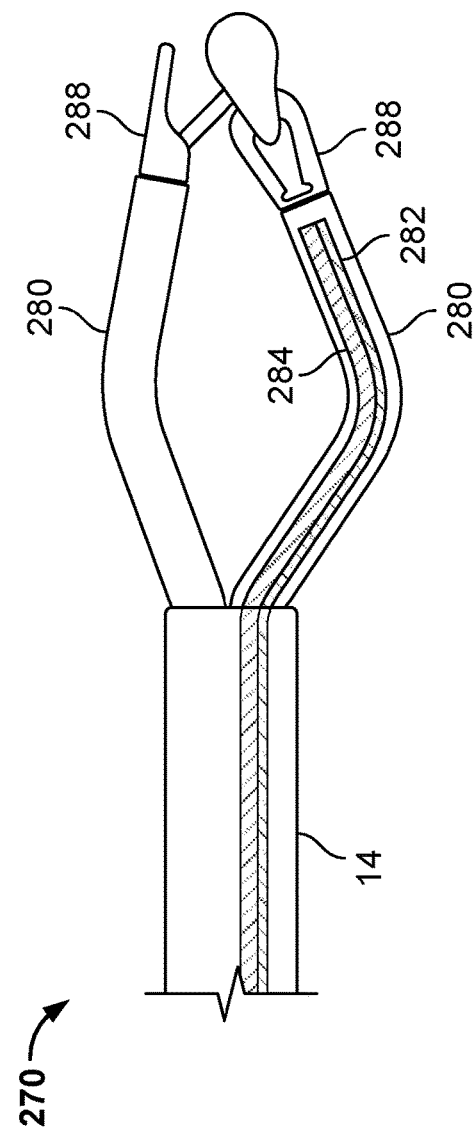
FIG. 8B is another side view of the surgical instrument assembly of FIG. 8A.

Referring now to FIGS. 8A and 8B, an exemplary surgical instrument assembly 270 is shown. In various example embodiments, surgical instrument assembly 270 includes one or more features of surgical instrument assembly 100, described above with reference to FIGS. 1-4. Surgical instrument assembly 270 has arms 280 that include a spring metal insert 282 and an inflatable channel 284. The spring metal insert 282 and/or inflatable channel facilitate manipulation and operation of the arms 280 and end effectors 288.

An outer bend profile 286 is illustrated in FIG. 8A. The bend profile 286 shows a resting state of the spring metal insert (e.g., due to the memory shaped profile). Extension of the arms 280 results in curvature of the arms 280 induced by the memory shaped profile of the spring metal. The arms 280 are straightened when retracted into the working channel 14 (e.g., stressing the spring metal insert 282 into a straightened configuration).

The inflatable channel 284 is selectively pressurized via variable hydraulic control to manipulate the arms 280 and/or end effectors 288. In an example embodiment, the inflatable channel is pressurized to straighten arm 280 (e.g., overcoming the memory shaped spring metal insert 282), and depressurized or relaxed to allow arm 280 to bend (e.g., by conforming to the memory shaped spring metal insert 282). Alternatively or additionally, the inflatable channel facilitates actuation of the end effector 288, such as by closing/gripping/cutting when pressurized (e.g., to a variable actuation force). In some embodiment, inflatable channel 284 includes two or more lumens that are at least partially independently controllable to facilitate manipulation of arm 280 and end effector 288 or to facilitate multiple functions of arm 280 and/or end effector 288.

FIGS. 9A and 9B illustrate an exemplary embodiment including a surgical instrument assembly having arms 300. Control of the arms 300 is facilitated by opposing forces of one or more components of the arms 300. In an example embodiment, arms 300 include a spring metal insert 302 and a nitinol insert 304. The spring metal insert 302 and the nitinol insert 304 are configured to control articulation of the arms 300 by using opposing forces induced in the spring metal insert and/or nitinol insert. For example, the nitinol insert 304 is shaped to have an outer bend profile that exhibits a predefined curvature in a resting (e.g., unstressed) state, illustrated in FIG. 9A. The force exerted by the nitinol insert 304 causes the arm 300 to bend to the outer profile. For example, the force generated by the nitinol insert 304 is greater than a force generated by the spring metal insert 302 (e.g. to return to a straightened configuration). The nitinol insert 304 is connected to an electricity source that electrifies and/or heats the nitinol insert 304. Electrification of the nitinol insert 304 can be variably controlled to selectively relax the nitinol insert 304 when electrified/heated. In the relaxed state, the nitinol insert 304 exerts a relatively weaker force against the spring metal insert 302, or is biased to a straightened configuration, such that the arm straightens into the configuration illustrated in FIG. 9B.

Utilizing opposing forces to selectively curve arm 300 can facilitate precise control in a relatively compact outer diameter, and/or can reduce the number of moving parts for manipulation of arm 300. In an example embodiment, the memory shaped curvature of the insert 304 can be selected to exhibit a desired shape in a resting state, which can be selectively varied through electrification, heating, etc. of one or both inserts 302, 304 to achieve a precisely controllable range of movement and orientations within a small anatomical target location and via a small diameter working channel.

Various example surgical instrument assemblies described herein utilize one or more end effectors to facilitate operation within a target anatomical location. Referring now to FIGS. 10A to 10I, end views of embodiments of grasping end effectors of the surgical instrument assembly are shown. In various example embodiments, one or more end effectors shown in FIGS. 10A to 10I are implemented in surgical instrument assembly 100 described above (e.g., alternatively or additionally to one or more features of end effectors 110 extending from each arm 108 described with reference to FIG. 1). Accordingly, in various example embodiments, each arm 108 can include one or more of the end effectors shown and described herein.

FIG. 10A illustrates an end effector 301 that includes a hook 310 and a jaw 312 extending outwardly from working channel 14. The hook 310 and the jaw 312 are each movable longitudinally independent of one another such that the hook 310 and the jaw 312 can both extend distally from the arm 108 and can be retracted proximally to be received within arm 108. Hook 310 includes a recessed area 314 defined by the structure of the hook 310. In an example embodiment, the hook 310 includes a shaped rod having angled wall sections 310a and 310b proximate a distal end that define recessed area 314. Alternatively or additionally, hook 310 includes, curved walls, a recess, or other shape, that defines recessed area 314. In an example embodiment, the hook 310 and jaw 312 have a different shape such that hook 310 is not symmetrical with jaw 312 (e.g., jaw 312 is relatively flatter compared to hook 310).

The recessed area 314 is sized to at least partially accommodate and/or retain a target 316 (e.g., target tissue for biopsy, treatment, etc.) between the hook 310 and the jaw 312. In an example embodiment, the jaw 312 is angled away from a proximal portion of the hook 310 (e.g., that extends along a longitudinal axis substantially parallel to a working channel). Such an angle can result in the hook being angled or offset, providing space for the jaw 312 to extend distally past hook 310 and/or providing space for the target 316 to be held between the hook 310 and the jaw 312. In various example embodiments, the target 316 is located within a surgical treatment area, such as a lung accessed during a biopsy operation, and includes a tissue, tumor, foreign object, plaque, abnormal tissues, or other target that can be encountered by the surgical instrument assemblies described herein.

In an example embodiment, the target 316 can be grasped while the hook 310 is extended longitudinally a greater distance than the jaw 312. The hook 310 is then moved relative to the jaw 312 to trap or otherwise secure the target 316 at least partially between the hook 310 and the jaw 312. In an example embodiment, the hook 310 is retracted in a longitudinal direction (e.g., of arrow A) relative to jaw 312. In some example embodiments, end effector 301 is thus actuated by sliding relative movement between hook 310 and jaw 312 (e.g., alone or in addition to articulating motion between hook 310 and jaw 312).

FIG. 10B illustrates a vacuum end effector 320 that can manipulate and/or grasp a target using suction. In an example embodiment, end effector 320 includes one or more hollow fluid channels 322 that pull fluid inward to create suction force at a suction side 324 of the vacuum effector 326. The fluid channels 322 are operatively connected to a pressure source at the control assembly 102 that provides negative pressure/suction (e.g., negative pneumatic or hydraulic pressure/suction) through the fluid channels 322. For example, one or more lumens extend from the end effector 320, through the arm, and to the vacuum source. The pneumatic pressure through the fluid channels 322 generates a resulting force that is controllable to selectively pull a target against the suction side 324 of the vacuum effector 320.

In an example embodiment, the vacuum effector 320 includes a single suction side 324. Outermost openings of the channels 322 are oriented perpendicular (e.g., substantially perpendicular, within about 10 degrees of exactly perpendicular) to a longitudinal axis of the working channel 14 and/or arm of the surgical instrument device. Alternatively or additionally, vacuum effector 320 can include two or more suction sides 324 that can be positioned on multiple sides of the vacuum effector 320 or that extend around a portion or all of the vacuum effector 320. In an example embodiment, outermost openings of the channels 322 are oriented parallel (e.g., substantially parallel, within about 10 degrees of exactly parallel) to a longitudinal axis of the working channel 14).

Vacuum effector 320 facilitates relatively few or no moving parts (e.g., at the end effector within the target anatomical location during use). In some embodiments, relatively few or no moving parts can facilitate a vacuum effector 320 that is relatively compact such that it can be deployed in small anatomical spaces through working channel 14 via arm 108.

In various example embodiments, the vacuum effector 320 is manufactured via additive manufacturing (i.e. three-dimensional printing). Additive manufacturing facilitates construction of various shapes and profiles that can be tailored to a particular target anatomical region, type of operation, and/or to generate a predetermined suction profile (e.g., tailored to a particular target).

FIG. 10C illustrates a hook end effector 330 that can manipulate and/or grasp a target via a grasping hook 332. One or more grasping hooks 332 are positioned along at least a portion of a length of the end effector 330. For example, the grasping hooks 332 are positioned along one side of the hook end effector 330. Each grasping hook 332 extends away from hook end effector 330 and curves proximally at an angle (e.g., at or about 90 degrees). The proximal curvature of the gasping hooks 332 facilitates distal advancement of the end effector 330 (e.g. via manipulation of control assembly 102) without grasping and/or resistance against a target or tissue in the target area. Retraction of the end effector 330 (e.g. via manipulation of control assembly 102 to retract the end effector 330 proximally into the arm 108) facilitates engagement between the grasping hooks 332 and the target to retract the target with the end effector 330. In some embodiments, the curved or angled shape of the grasping hooks 332 can promote secure engagement with the target for extraction (e.g., such that the target remains engaged with the end effector 330 until removed from the patient).

In an example embodiment, the grasping hooks 332 are arranged around less than an entire circumference of the end effector 330 (e.g., on a single side of the end effector 330). Such a configuration can facilitate precise engagement with a target located proximate a single side of the end effector 330. In some example embodiments, the grasping hooks 332 are positioned along both sides of the hook end effector 330 (e.g. extending outwardly in at least partially opposed directions). Such a configuration can facilitate a larger grasping area. Alternatively or additionally, multiple grasping hooks 332 are arranged in a spiral, linear, offset, or other pattern around some or an entire circumference of end effector 330.

Alternatively or additionally, end effector 330 includes one or more grasping barbs 333. In an example embodiment, each grasping barb 333 has angled surfaces that are oriented in a proximal direction. Such an orientation of the gasping barbs 333 can facilitate distal advancement of the end effector 330 without grasping and/or engagement with a target or tissue in the target area. Retraction of the end effector 330 proximally facilitates engagement between the grasping barbs 333 and the target to retract the target with the end effector 330. In an example embodiment, grasping barbs 333 are positioned at the end of the end effector 330.

In an example embodiment, the grasping barbs 333 are arranged around less than an entire circumference of the end effector 330 (e.g., on a single side of the end effector 330). Such a configuration can facilitate precise engagement with a target located proximate a single side of the end effector 330. In some example embodiments, the grasping barbs 333 are positioned along both sides of the hook end effector 330 (e.g. extending outwardly in at least partially opposed directions). Such a configuration can facilitate a larger grasping area. Alternatively or additionally, multiple grasping barbs 333 are arranged in a spiral, linear, offset, or other pattern around some or an entire circumference of end effector 330.

In various example embodiments, end effector 330 can include one or more grasping features, including rounded hooks, pointed hooks having a sharp edge or point, barbs, etc. For example, the shape and characteristics (i.e. rounded, curved, pointed, barbs, etc.) of the grasping hooks can be selected based on the tissue characteristics in the target area, such as the force required to engage a target and/or remove the target from its anatomical location.

In an example embodiment, the grasping hooks and/or barbs 332, 333 are located in a fixed position. For example, the grasping hooks and/or barbs 332, 333 are affixed to permanently extend outwardly from the end effector. Such a configuration can limit moving parts associated with the grasping hooks and/or barbs 332, 333, facilitating efficient manufacturing and reliability during operation. Alternatively or additionally, the grasping hooks and/or barbs 332, 333 can be movable relative to other portions of the end effector 330. For example, one or more grasping hooks and/or barbs 332, 333 can be selectively retracted at least partially into the end effector 330 (e.g., via manipulation of a control assembly by the operator). Retracting at least partially within the end effector 330 can facilitate advancement or movement of end effector 330 to a target, and selectively extend from the end effector 330 to facilitate engagement with the target. In some embodiments, the selective retraction can also facilitate secure engagement with the target, such as by partially retracting the grasping hooks and/or barbs 332, 333 after engagement with the target to exert additional force on the target during removal.

Figure 10E:
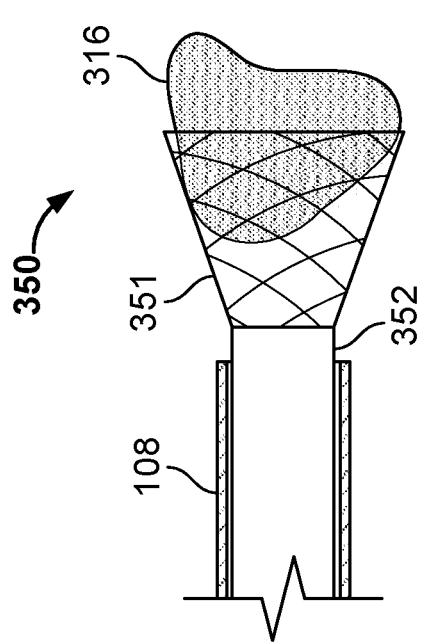
Figure 10E:
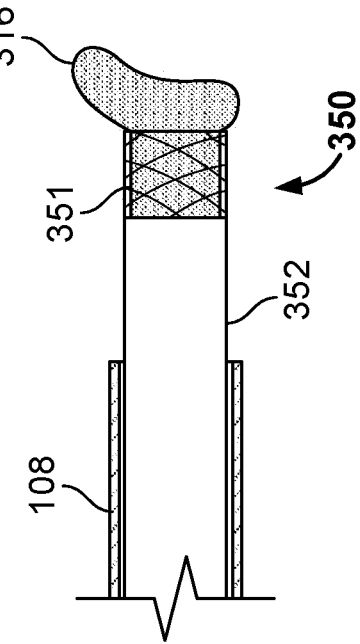
Figure 10D:
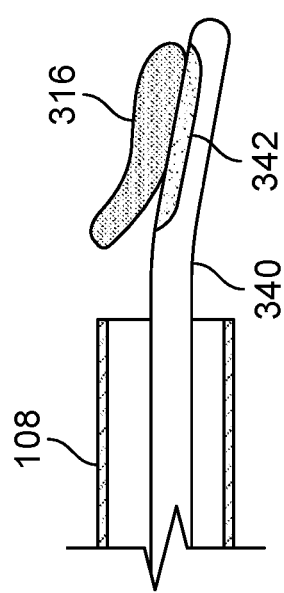

FIG. 10D illustrates an adhesive end effector 340 that can manipulate and/or grasp a target using an adhesive surface. The adhesive end effector 340 includes a tacky substrate 342 applied to the adhesive end effector 340 that allows the target 316 to adhere to the substrate 342 for manipulation by adhesive end effector 340. Adhesive end effector 340 is angled to provide an angled surface at which the tacky substrate 342 is located applied. For example, end effector 340 is retained within arm 108 until arm 108 is positioned at a target area, and the end effector 340 is distally advanced out of the distal end of arm 108 (e.g. via manipulation of control assembly 102) to expose the adhesive end effector 340 in the target area. Exposure of the tacky substrate 342 facilitates adherence to a target (e.g. target 316) that can be retracted proximally with the end effector 340 (e.g. via manipulation of control assembly 102) and retained within arm 108 for removal from the target area. In various example embodiments, tacky substrate 342 is included together with one or more other features of end effectors described herein.

FIG. 10E illustrates an end effector 350 that can be selectively expanded and collapsed to capture and retain a target. In an example embodiment, the end effector 350 includes a basket 351 that can be selectively expanded and collapsed. For example, basket 351 collapses into the arm 108 when retracted proximally relative to the arm and expands outwardly (e.g., by radially deflecting outwardly) when advanced distally out of the arm 108. In an example embodiment, the end effector 350 is movable relative to a cannula 352. The basket 351 and cannula 352 are movable relative to one another such that the basket can be expanded or collapsed at a variety of longitudinal positions relative to a distal portion of the arm 108. The basket 351 is a nitinol stent basket that can capture one or more targets (e.g. target 316). The arm 108 can be advanced distally over the basket 351 which can cause the basket 351 to collapse and retain or retrieve the target 316 captured by the basket 351.

Figure 10F:
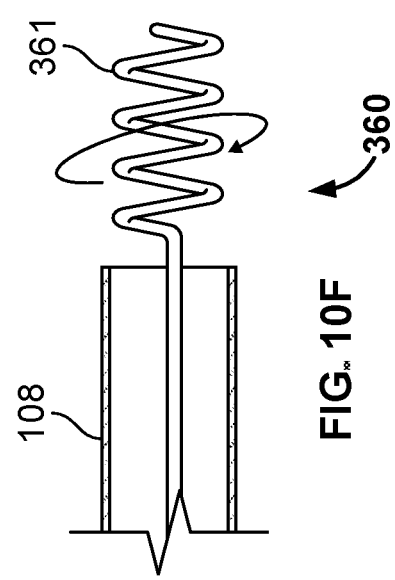

FIG. 10F illustrates an end effector 360 that is rotatable to engage a target. In an example embodiment, the end effector 360 can be manipulated to provide both longitudinal movement and rotation within a target area (e.g., the end effector 360 is rotatable in clockwise and counter clockwise directions via manipulation at control assembly 102) to retain a target within arm 108. For example, end effector 360 includes a corkscrew shaped wire 361 positioned at a distal end of end effector 360. Rotation of the end effector 360 rotates corkscrew 361. End effector 360 can be extended longitudinally into a target area to extend distally from the distal end of arm 108 to expose corkscrew 361. The end effector 360 is rotated to rotate the corkscrew 361, which allows corkscrew 361 to embed into a target (e.g. target 316) that can be retained or removed within arm 108. Alternatively or additionally, rotation or other manipulation of end effector 360 engages the target by capturing the target at least partially within the space between portions of the corkscrew shaped wire (e.g., without embedding into the tissue).

Figure 10H:
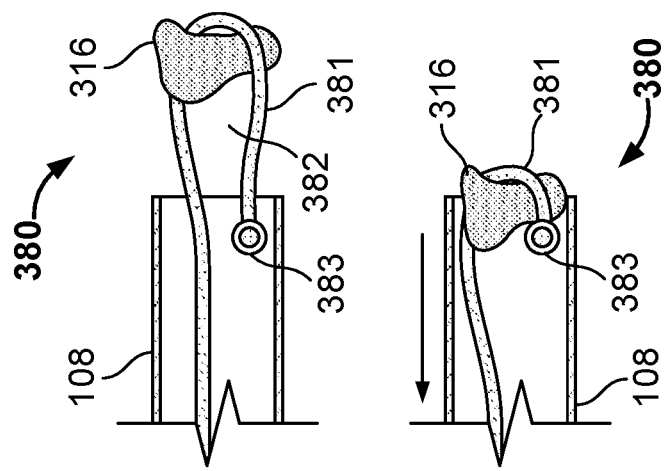
Figure 10G:
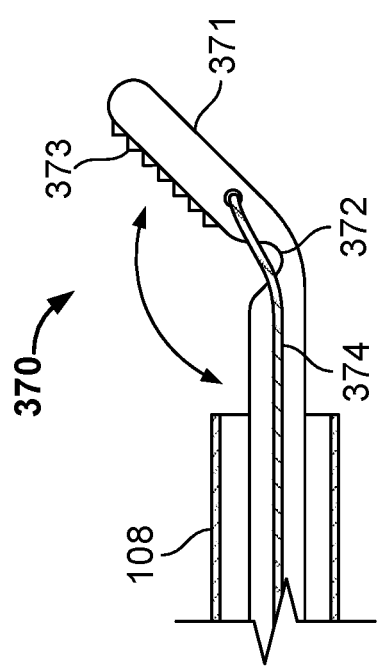

FIG. 10G illustrates an end effector 370 that includes a hinged mechanism for grasping a target within a target area. End effector 370 includes a jaw 371 that includes a compliant hinge 372 actuated by hinge wire 374 (e.g. via manipulation of control assembly 102). Hinge wire 374 controls the orientation of the jaw 371 via control of flexure hinge 372, by actuating the jaw 371 between an extended open position where the jaw 371 deflects distally away from arm 108. The hinge wire 374 retracts and pulls the jaw 371 into a closed position where the jaw 371 proximally rotates about hinge 372 toward a distal end of arm 108.

In an example embodiment, hinge 372 is biased towards the extended open position. Tensioning of hinge wire 374 overcomes the bias force and causes the hinge 372 to flex, drawing the jaw 371 proximally into the closed position. Loosening of hinge wire 374 allows the jaw 371 to move towards the extended open position due to the bias force of the hinge 372.

In an example embodiment, hinge 372 is formed of a compliant material, such as a living hinge formed of an area of reduced material thickness or increased compliance/flexibility. Alternatively or additionally, hinge 372 can include multiple components that articulate relative to one another, such as a pin hinge.

End effector 370 includes one or more features that facilitate engagement with a target. In an example embodiment, end effector includes an engagement surface 373 that includes teeth, textured surface, tacky substrate, etc. The engagement surface 373 can be manipulated to selectively contact the target. Alternatively or additionally, end effector 370 includes one or more jaw portions, such as a jaw portion that remains in a fixed position relative to jaw 371 while hinge 372 is flexed. Such a fixed feature can facilitate grasping of a target (e.g., due to additional frictional engagement with engagement surface 373 of jaw 371.

FIG. 10H illustrates an end effector 380 that can manipulate and/or grasp a target via a loop. End effector 380 includes a wire or fiber loop 381 that is configured for longitudinal movement (e.g. via manipulation at control assembly 102). The loop 381 is advanced past the distal end of the arm 108 to expose an opening 382 defined by the loop 381. The size of the opening 382 is adjustable with the advancement of the loop 381. By extending further distally, the opening 382 becomes larger. During use, the opening 382 is selectively sized by the operator to at least partially surround a target (e.g. target 316). The loop 381 is then retracted relative to the arm 108, and the loop 381 tightens around the target 316 to retrain the target within the arm 108.

Manipulation of the loop is facilitated by an anchor location 383. For example, a distal end of the loop 381 is anchored at a fixed location proximate a distal end of arm 108. Extension and retraction of loop 381 thus facilitates increasing and decreasing the size of loop 381, respectively, while an end remains in a fixed position at anchor location 383.

Figure 10I:
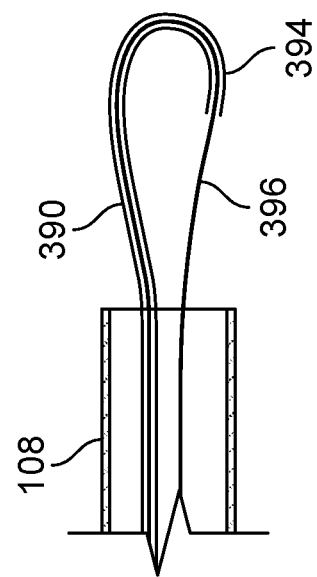

FIG. 10I illustrates an end effector 390 that can manipulate and/or grasp a target using a loop that extends into a target area. For example, end effector 390 includes a compliant hooked cannula 394 that includes a channel that a wire 396 passes through. The compliant hooked cannula 394 is configured for longitudinal movement distally and proximally in relation to arm 108 (e.g. via manipulation at control assembly 102). Wire 396 passes through the cannula 394 and is retained within the cannula 394. Wire 396 facilitates grasping of a target (e.g. target 316) against the compliant hooked cannula 394, and the hooked cannula 394 is retracted within arm 108 to retain target 316.

FIGS. 11A to 11E illustrate example embodiments of cutting end effectors that include one or more features for cutting target tissue. In various example embodiments, end effectors of FIGS. 11A to 11E are implemented in surgical instrument assembly 100 described above, and used in conjunction with one or more features of surgical instrument assemblies described herein (e.g., by incorporating end effectors 110 to extend from each arm 108 illustrated in FIG. 1. Accordingly, in an example embodiment, each arm 108 includes one or more of the end effectors shown and described herein.

Figure 11A:
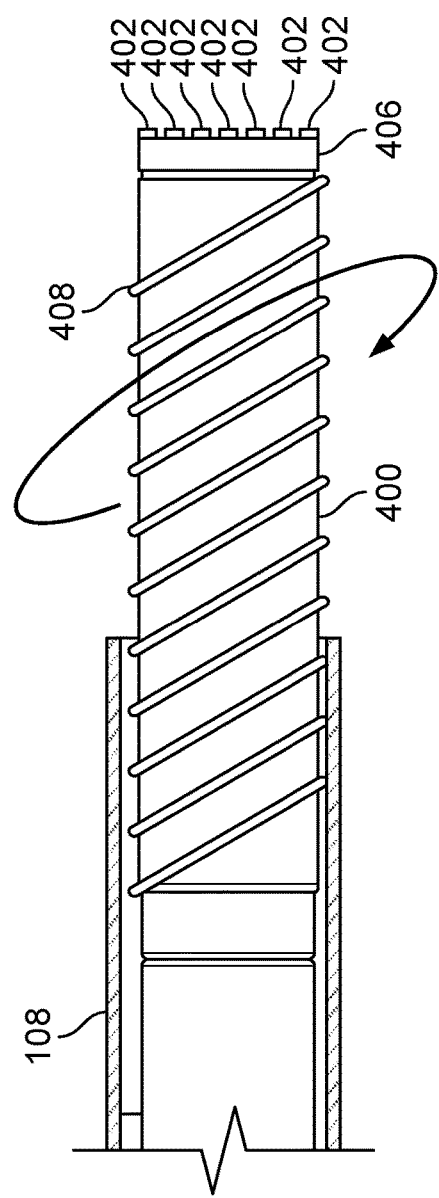
FIGS. 11A to 11E illustrate various end views of embodiments of cutting end effectors of surgical instrument assemblies.
Figure 11B:
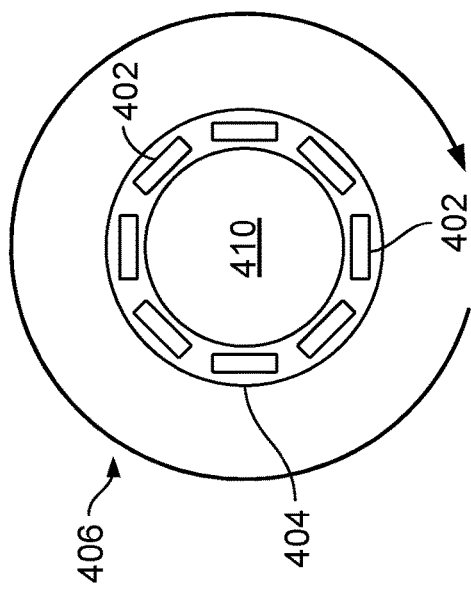

FIGS. 11A and 11B illustrate an example cutting effector 400 that manipulates and/or cuts a target. Cutting effector 400 includes a coring tool that has cutting surfaces 402 positioned around at least a portion of a circumference 404 of a distal end 406 of the cutting effector 400. In an example embodiment, the distal end 406 is substantially perpendicular to a longitudinal rotational axis of the cutting effector 400, and the cutting surfaces include blades extending from the distal end 406 in a direction parallel to the longitudinal rotational axis.

The cutting effector 400 includes threads 408 that facilitate longitudinal movement of the cutting effector 400 relative to the arm 108. In an example embodiment, the threads 408 interact with complementary features or threads on an internal surface of the arm 108. The cutting effector is extended and retracted by rotating the cutting effector 400 via a threaded engagement with arm 108 (e.g. via manipulation at control assembly 102 to control rotation).

In an example embodiment, the cutting effector 400 is retained within arm 108 (e.g., and is not exposed) during advancement of arm 108 to the target area. When the arm 108 is located proximate the target area, cutting effector 400 is extended outwardly relative to arm 108 to expose the cutting surfaces 402 to the target area. In an example embodiment, the cutting surfaces 420 cut the target area while cutting effector is rotated. The cutting surfaces 402 rotate and advance, while rotation of cutting effector 400 facilitates cutting of the target area. In some embodiments, rotating cutting surfaces 420 can facilitate precise and consistent extraction of a target. For example, the arm 108 can be advanced into contact or in close proximity to the target while the cutting effector 400 is retained partially or entirely within the arm 108. The cutting effector 400 can then be rotated to advance the cutting effector 400 into the target while the cutting surfaces 402 operate to cut. The target can be retained within the internal chamber 410 for extraction.

Alternatively or additionally, the cutting surfaces 402 are configured to cut the target area without rotation. For example, cutting surfaces 402 are actuated into contact with the target area and cut the target area via pressure between the cutting surfaces 402 and the target area (e.g., without continuous rotation during engagement with the target).

The cutting effector 400 is at least partially hollow to define the internal chamber 410. In an example embodiment, the internal chamber is at least partially accessible proximally, such that additional end effectors (e.g. effectors for grasping, imaging, cutting, etc.) can be positioned through the cutting effector 400. Cutting effector 400 can thus accommodate one or more complementary end effectors (e.g., that can be used to facilitate removal of a target alone or together with cutting effector 400).

Figure 11C:
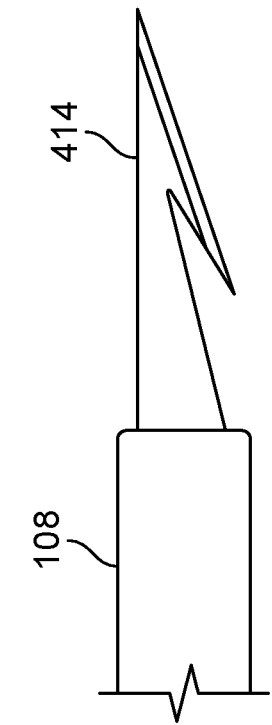
Figure 11D:
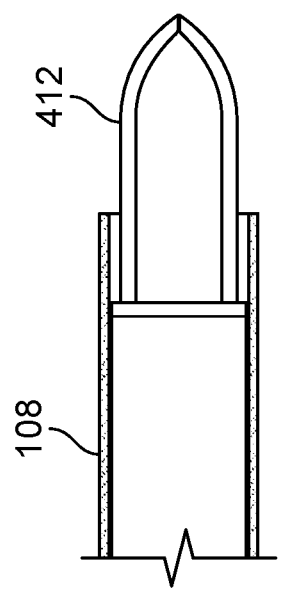

FIGS. 11C and 11D illustrate example cutting effectors 412 and 414 that manipulate and/or cut a target. Cutting effectors 412, 414 include scalpel blades. In an example embodiment, scalpel blades of cutting effectors 412, 414 have a compact, low profile to facilitate retraction at least partially within arm 108, and passage through a relatively small working channel.

Cutting effectors 412, 414 are configured for longitudinal movement controlled by control assembly (e.g. via manipulation of control assembly 102 by an operator). In an example embodiment, thee cutting effector 412, 414 is retained within arm 108 (e.g., and are not exposed) during advancement of arm 108 to the target area. When the arm 108 is located proximate the target area, cutting effector 412, 414 is extended outwardly relative to arm 108 to expose the cutting surfaces 402 to the target area. The arm 108 and/or cutting effector 412, 414 can be manipulated by the operator to cut the target.

In an example embodiments, cutting effectors 412, 414 include radio frequency energy that is controlled (e.g. by control assembly 102) to bolster the cutting functionality of cutting effectors 412, 414. For example, radio frequency can be transmitted via the cutting effectors 412, 414 to enhance operation of the cutting effectors 412, 414 and/or to operate on the target us radio frequency energy.

Cutting effectors 412, 414 include a cutting profile having at least one cutting edge. In an example embodiment, cutting effector 412 includes curved cutting edges that culminate in a distal tip. Cutting effector 414 includes an angled cutting surface and a barbed profile that facilitates cutting in multiple directions and/or engagement with tissue via the barbed profile. Such shapes can facilitate precise manipulation of the blade in a small target anatomical location, and controlled cutting of the target.

Figure 11E:
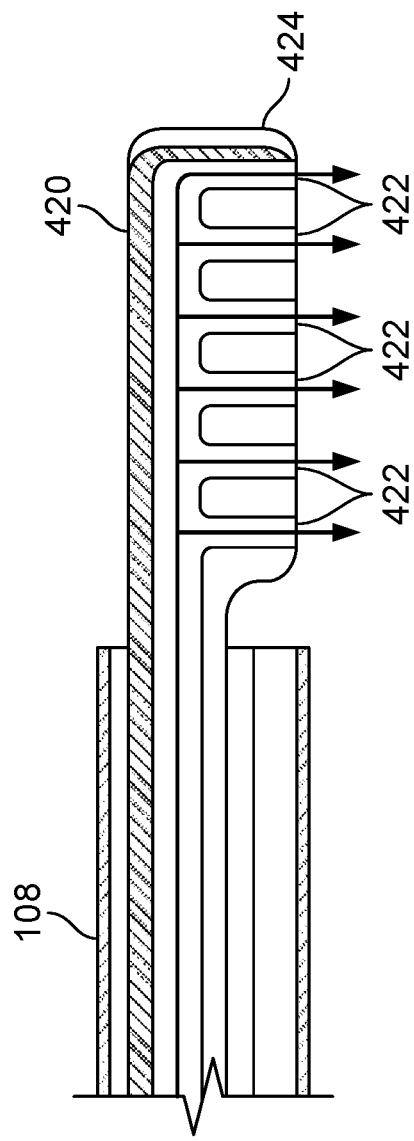

FIG. 11E illustrates and exemplary embodiment of a cutting effector 420 that can manipulate and/or cut a target. In an example embodiment, cutting effector 420 utilizes one or more of chemical dissection, cryo-freeze, and/or steam to operate on a target. In an example embodiment, cutting effector 420 includes hollow fluid channels 422. A fluid is controllably passed through the hollow fluid channels 422 towards the target too cut, burn, freeze, or otherwise manipulate the target. For example, end effector 420 delivers a fluid through fluid channels 422 at a high pressure and/or temperature to exert an outward pressure at a cutting side 424 of the cutting effector 420 onto the target. The fluid channels 422 can be connected to a pressure source at the control assembly 102 that provides pressure (e.g. hydraulic, pneumatic, etc.) through the fluid channels 422. For example, one or more lumens extend from the end effector 420, through the arm, and to the pressure source. The pressure through the fluid channels 422 generates a resulting force that manipulates and/or cuts a target (e.g. target 316).

Alternatively or additionally, end effector 420 produces a low temperature that operates on the target by freezing the target (e.g., to remove or otherwise treat the target). For example, a fluid having an extremely low temperature (e.g., liquid nitrogen) is delivered to the target via fluid channels 422 to selectively treat the target with low temperature.

The cutting effector 420 has one or multiple cutting sides 424. For example, the cutting effector 420 has a single cutting side 424. Alternatively or additionally, cutting effector 420 includes two or more cutting sides 424 positioned on multiple sides of the cutting effector 420. In some example embodiments, cutting effector 420 provides limited moving parts, promoting a compact overall size that can be deployed in small anatomical spaces through arm 108 and a relatively small working channel.

In various example embodiments, the end effector 420 is manufactured via additive manufacturing (i.e. three-dimensional printing). Additive manufacturing facilitates construction of various shapes and profiles that can be tailored to a particular target anatomical region, type of operation, and/or to generate a predetermined suction profile (e.g., tailored to a particular target).

FIGS. 12A to 12L illustrate example embodiments of end effectors that include one or more features for cutting and/or grasping target tissue. In various example embodiments, end effectors of FIGS. 12A to 12L are implemented in surgical instrument assembly 100 described above, and used in conjunction with one or more features of surgical instrument assemblies described herein (e.g., by incorporating end effectors to extend from each arm 108 illustrated in FIG. 1). Accordingly, in an example embodiment, each arm 108 includes one or more of the end effectors shown and described herein.

Figure 12C:
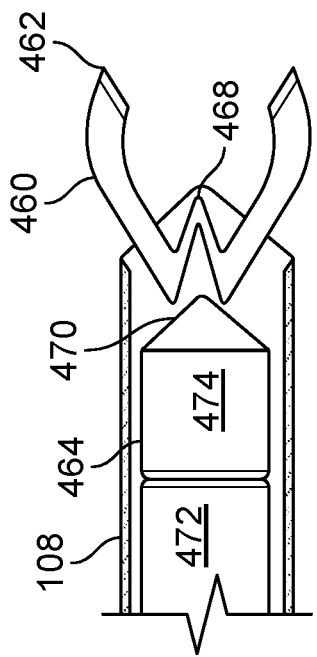
Figure 12D:
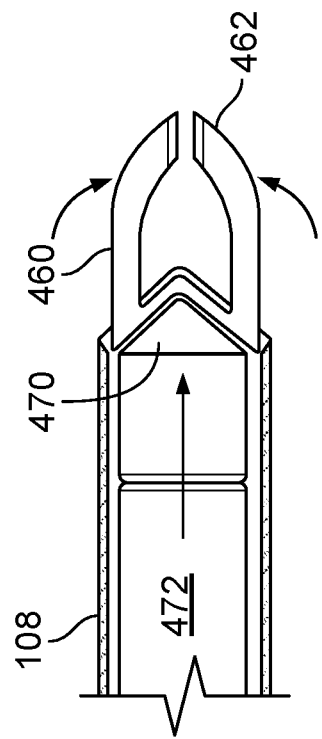
Figure 12A:
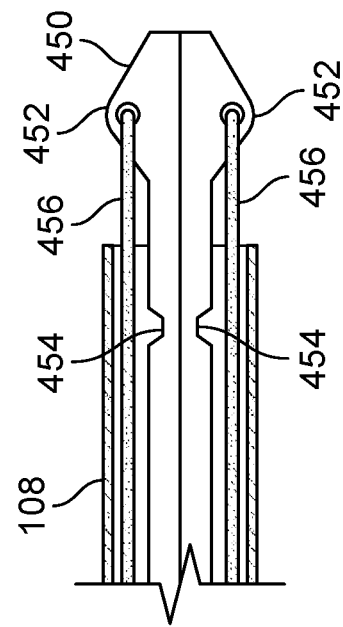
Figure 12B:
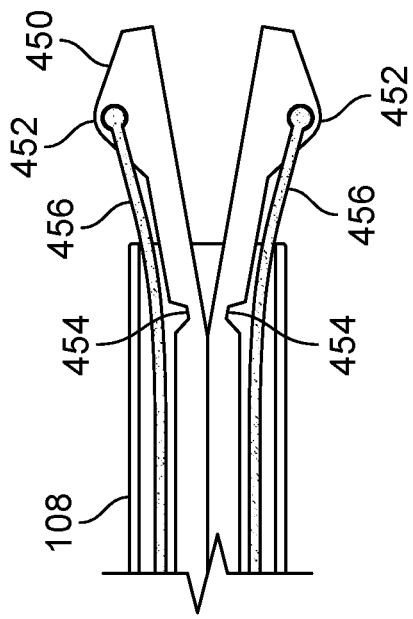

FIGS. 12A and 12B illustrate a compliant hinge effector 450 that is configured to grasp and/or cut a target. The end effector 450 includes a flexure mechanism having a compliant flexure hinge 454 that facilitates deflection of the end effector. In an example embodiment, the end effector 450 has opposing arms or jaws 452, each having a compliant flexure hinge 454 that allows the opposing arms or jaws to deflect towards and away from each other. One or both opposing arm 452 connected (directly or indirectly) to an arm wire 456 that extends through working arm 108. The arm wires 456 control the flexure position of each arm 452 (e.g. via manipulation at control assembly 102). The compliant hinge effector 450 is configured for longitudinal movement in relation to arm 108, and the longitudinal position of the compliant hinge effector 450 controls the distance each arm 452 can deflect outwards. For example, with compliant hinges 454 positioned within arm 108, arms 452 are able to deflect to an outer position (e.g. as shown in FIG. 12B). Distal longitudinal movement of compliant hinge effector 450 to position compliant hinges 454 out of the distal end of the arm 108 provides additional flexibility for the arms 452 to deflect outward.

In an example embodiment, hinges 454 are biased to return the end effector to a closed configuration (e.g., FIG. 12A). Tensioning of arm wire 456 at least partially overcomes the bias force and causes the hinges 454 to flex, drawing the arms towards a closed position (e.g., FIG. 12B).

In an example embodiment, compliant hinges 454 are formed of a compliant material, such as a living hinge formed of an area of reduced material thickness or increased compliance/flexibility. Alternatively or additionally, hinge 454 can include multiple components that articulate relative to one another, such as a pin hinge.

FIGS. 12C and 12D illustrate end effector 460 that is configured to grasp and/or cut a target. End effector 460 includes a set of spring metal jaws 462 and an actuator 464. The spring metal jaws 462 are formed in a W-shape that includes a central fulcrum 468 positioned between the two jaws 462. The fulcrum 468 is longitudinally aligned with a tip 470 of actuator 464. Actuator 464 has a body portion 472 that is cylindrical in shape and a tip portion 474 that tapers from a cylindrical body to a conical shape that includes the tip 470 at the distal end. Actuator 464 is translated in proximal and distal directions (e.g. via manipulation at control assembly 102). When translated in the distal direction the actuator 464 contacts the spring metal jaws 462, applying a force that causes the jaws to rotate (e.g., at fulcrum 468) towards a closed configuration (FIG. 12D). In an example embodiment, the jaws 462 are biased towards an open position (e.g., FIG. 12C). Accordingly, when the actuator 464 is located proximally spaced away from the spring metal jaws 462, the jaws 462 are in an open position.

The actuator 464 is manipulated (e.g., via the control assembly 102) to move longitudinally at least partially within arm 108. In an example embodiment, the actuator 464 is movable via hydraulic or pneumatic pressure that can be manipulated using control assembly 102. Alternatively or additionally, actuate 464 is movable mechanically using one or more wires, threaded engagement with arm 108, etc.

Figure 12G:
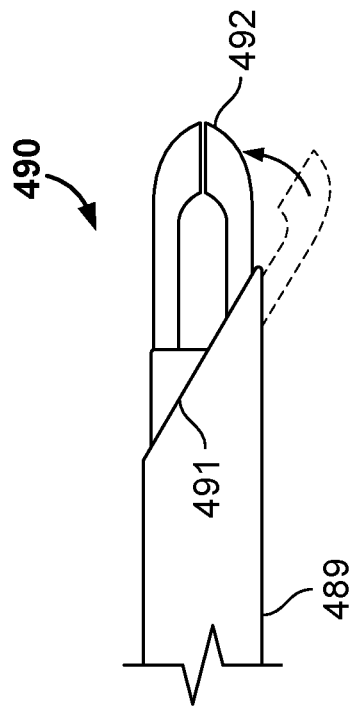
Figure 12H:
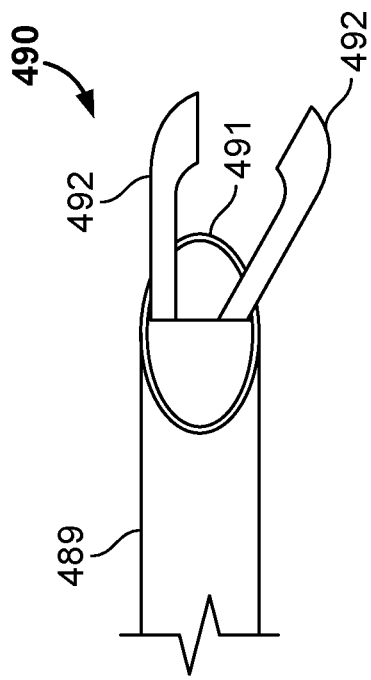
Figure 12E:
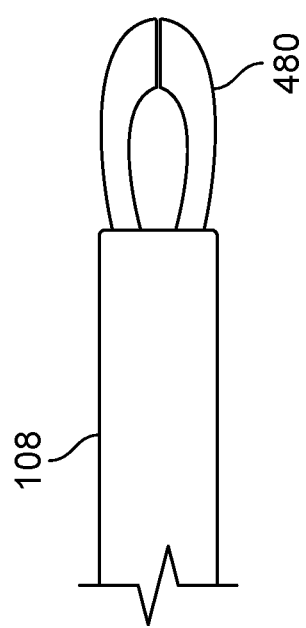
Figure 12F:
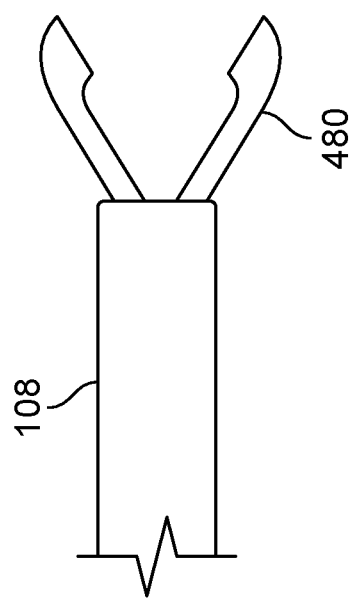

FIGS. 12E and 12F illustrate an example of a forceps effector 480 that is configured to grasp and/or cut a target. The forceps effector 480 includes nitinol memory metal that can be actuated using temperature and/or electrification (e.g. via manipulation at control assembly 102). The forceps effector 480 includes a first configuration in which the effector 480 is in a closed or clamped configuration (e.g., FIG. 12E). The forceps effector 480 includes a second configuration in which the forceps effector 480 is in an open configuration (e.g., FIG. 12F). In an example embodiment, the forceps effector 480 is in the closed or clamped configuration when in a cooled or rested state, and is adjusted to the open configuration by heating or electrification. For example, the forceps effector 480 is adjusted into a relaxed state when the effector 480 (e.g., nitinol metal of effector 480) is heated by an electrical charge. In some embodiments, an internal body temperature of a subject in which the surgical instrument assembly 100 is deployed can assist in the shape memory changes of the forceps effector 480.

FIGS. 12G and 12H illustrate an exemplary effector 490 that includes jaws actuatable via rotation. The effector 490 includes an angled distal face 491 that provides an elliptical shaped distal opening. Jaws 492 can be controlled to extend at least partially from the angled distal face 491. The jaws 492 are biased into an open position (e.g., via a spring metal). In a first relative rotational positioning between jaws 492 and sleeve 489, the jaws 492 are constrained in a closed configuration (e.g., FIG. 12G). In a second relative rotational positioning between jaws 492 and sleeve 489, the jaws 492 are not fully constrained and move towards an open configuration (e.g., FIG. 12H). In some embodiments, manipulation of the jaws 492 is achieved without longitudinal translation of effector 492 or arm 108, and occurs via relative rotation only.

In an example embodiment, the actuation of twist sleeve 489 can be driven by a cam force via manipulation at control assembly 102. For example, the twist sleeve 489 is rotated at least partially over the jaws 492, overcoming the force of the spring metal and closing the jaws 492. In some aspects the twist sleeve 489 can include a ⅛ rotation, ¼ rotation, ½ rotation, etc., to open and/or close the jaws 492. In some embodiments, only a single jaw 492 is biased to an open position, while the other jaw 492 remains in a fixed orientation between open and closed configurations.

FIGS. 12I and 12J illustrate an example end effector 500 that includes jaws 502 and a mechanical blade 504. Distal ends of the jaws 502 are rotatable (e.g., in medial and lateral directions). In an example embodiment, the jaws 502 are biased to an open configuration. When retracted (e.g., at least partially) within the arm 108, the jaws 502 are constrained from opening and are maintained in a closed position (e.g., FIG. 12J). When extended longitudinally relative to a distal end of arm 108 (e.g., such that a joint 501 is located distally of the distal end of arm 108), the jaws are no longer constrained and move towards an open position (e.g., FIG. 12I). The position of the jaws 502 is controlled by manipulation at the control assembly 102, such as by controlling the longitudinal position of the jaws 502 relative to the arm 108.

In an example embodiment, the jaws 502 are retained in arm 108 and/or in a medial position (e.g. as illustrated in FIG. 12J) during advancement of the arm 108 to the target area. When proximate the target area, the jaws 502 are deflected laterally to open the jaws 502 to grasp the target, and the target is held by the jaws 502.

Alternatively or additionally, end effector 504 includes a blade 504. The blade 504 can be used to cut or otherwise operate on a target. The blade 504 is movable longitudinally relative to the arm 108 and/or jaws 502. In an example embodiment, the blade 504 is movable independently of the jaws 502 (e.g., when the jaws are in the open position). In some embodiments, the jaws 502 and blade 504 are movable in unison, such that movement of the jaws 502 result in a corresponding movement of the blade 504. For example, the jaws move towards the open configuration when the blade 504 is extended from the distal end of the arm 108.

When extended, the blade 504 can be used to cut the target (e.g. via manipulation at control assembly 102). The blade 504 is retracted after cutting is complete, and the jaws 502 deflect medially to cover the blade 504 and/or constrain a target for extraction.

In an example embodiment, the jaws 502 and mechanical blade 504 are arranged coaxially. Such an arrangement can facilitate larger components within arm 108, and/or facilitate positioning and control of both jaws 502 and blade 504 in a relatively small diameter arm 108.

FIGS. 12K and 12L illustrate an effector 510 that is actuated by relative longitudinal movement between first and second jaws 511, 514. In a first configuration (FIG. 12K), the jaws 511 and 514 are in an open configuration. For example, jaw 514 extends outwardly at an angle such that the first and second jaws 511 and 514 are at least partially separated from one another by a space. The jaws 511, 514 are movable into a second configuration in which the upper jaw 511 and lower jaw 514 are in contact with each other (e.g., FIG. 12L), by relative movement of the jaws 511, 514 and arm 108. For example, relative longitudinal movement of jaws 511, 514 into the arm 108 results in the jaws 511, 514 being deflected into the closed positon.

In an example embodiment, jaws 511, 514 are retained in the closed configuration during advancement of arm 108 to the target location. Proximate the target location, jaws 511, 514 are biased in a resting open position (e.g., FIG. 12K) by extending the jaws 511, 514 out of the arm 108 and/or retracting the arm 108 relative to jaws 511, 514. Grasping actuation to grasp a target is achieved by advancing the arm 108 in direction of arrow A (e.g., over an angled ramp 512 on the lower jaw 514). The angled ramp 512 facilitates the force from arm 108 against lower jaw 514, deflecting lower jaw 514 into contact with upper jaw 511.

Referring now to FIG. 13, an exemplary surgical assembly 530 is shown. In various example embodiments, surgical instrument assembly 530 includes one or more features of surgical instrument assembly 100 and/or various example effectors, described above with reference to FIGS. 1-12L. Surgical instrument assembly 530 includes an articulating imaging system 531 that facilitates imaging of a target area. The articulating imaging system 531 includes an articulation arm 532 and an imaging source 534 attached to the articulating arm 532 at a distal end. The imaging source 534 includes a camera, and/or a light based imaging source for use in optical microscopy, spectroscopy, endoscopy, scanning laser ophthalmoscopy, laser Doppler imaging, or optical coherence tomography. Alternatively or additionally, imaging source 534 captures imaging data via radiography, magnetic resonance imaging, nuclear imaging, ultrasound, elastography, photoacoustic imaging, tomography, echocardiography, functional near-infrared spectroscopy, magnetic particle imaging, and/or combinations thereof.

The articulating arm 532 extends from working channel 14 at a distal end of working channel 14, the articulating arm 532 is configured for longitudinal movement such that the articulating arm 532 can extend distally out of working channel 14 and be retracted proximally into working channel 14 (e.g. via manipulation at control assembly 102). The articulating arm 532 is retracted into an opening 536 in the working channel 14, the opening 536 is a slot in the distal end of the working channel that extends proximally away from the distal end to allow the articulating arm 532 to move in an axial direction away from the working channel 14. One or more wires (e.g. sensor wire 128) is/are connected to the articulation arm 532 to provide control of the positon of the articulation arm 532 from the control assembly 102. The articulation of articulation arm 532 provides flexibility to orient the imaging source 534 towards an area of operation that can include the arms 108 and end effectors 110 within a target area. In various example embodiments, movement of arm 532 is facilitated by one or more features described above with reference to arms 108 and/or effectors described with reference to FIGS. 10-12L.

Figure 14:
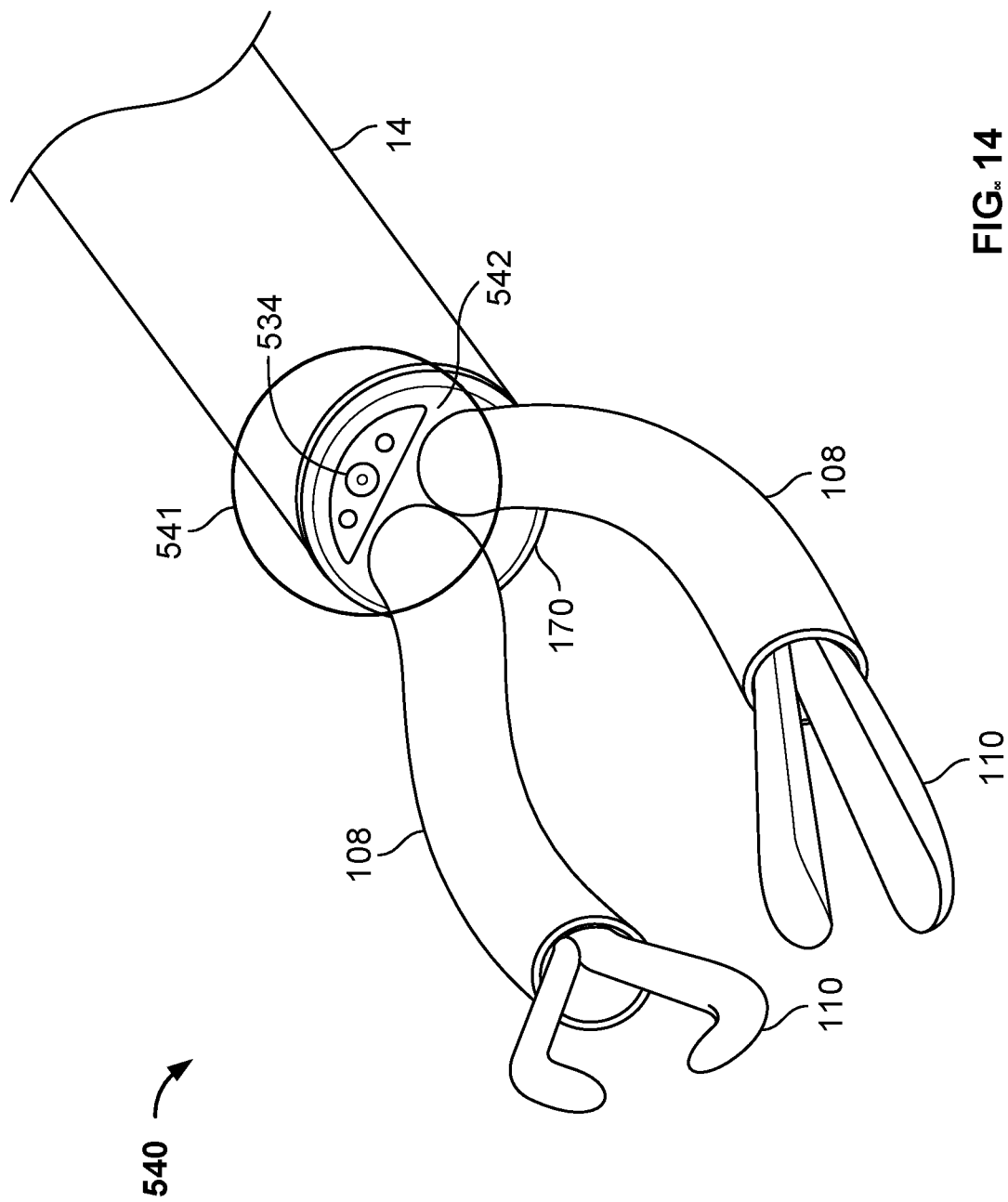
FIG. 14 illustrates a perspective view of an end of a surgical instrument assembly having another imaging system.

Referring now to FIG. 14, an exemplary surgical assembly 540 is shown. In various example embodiments, surgical instrument assembly 540 includes one or more features of surgical instrument assembly 100 and surgical instrument assembly 530, described above with reference to FIGS. 1-13. The fixed imaging system 541 includes imaging source 534 connected to the distal end 170 of an arm 542 positioned within working channel 14 at a fixed position. The fixed position of the imaging system 541 is oriented towards an area of operation that can include the arms 108 and end effectors 110. Such a configuration can facilitate a consistent perspective relative to the arms 108.

Referring now to FIG. 15, an exemplary surgical assembly 550 is shown. In various example embodiments, surgical instrument assembly 550 includes one or more features of surgical instrument assembly 100, surgical instrument assembly 530, and surgical instrument assembly 540, described above with reference to FIGS. 1-14. Surgical instrument assembly 550 includes an ultrasonic imaging system 551. The ultrasonic imaging system 551 includes a radial ultrasonic arm 552 that extends from the distal end 170 of the working channel 14. In some example embodiments, the radial ultrasonic arm 552 is introduced in place of the aspiration channel. Alternatively or additionally, surgical instrument assembly 550 includes both radial ultrasonic arm 552 and an aspiration channel. The radial ultrasonic arm 552 emits ultrasonic waves 554 that provide ultrasonic imaging from the ultrasonic imaging system 551.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. For example, features described in the context of an example, end effector, arm, or other feature, can be used in combination with one or more other end effectors, arms, or other features. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A surgical instrument assembly, comprising:
   a first arm having a proximal end and a distal end, a first end effector located at the distal end of the first arm, wherein the first end effector comprises jaws adjustable between an open configuration and a grasping configuration;
   a second arm having a proximal end and a distal end, a second end effector located at the distal end of the second arm; and
   a control assembly located at the proximal ends of the first and second arms, the control assembly including a first end effector input that actuates the first end effector, a second end effector input that actuates the second end effector, a first arm input that controls at least one degree of freedom of the first arm, and a second arm input that controls at least one degree of freedom of the second arm;
   wherein the first and second arms are configured to pass through a working channel having a diameter of 2 mm or less while the first and second arms and first and second end effectors are manipulated by the control assembly.

2. The surgical instrument assembly of claim 1, wherein the control assembly includes a first control assembly housing and a second control assembly housing that is separate from the first control assembly housing, the first control assembly housing comprising a first handle, the first arm input, and the first end effector input, and the second control assembly housing comprising a second handle, the second arm input, and the second end effector input.

3. The surgical instrument assembly of claim 2, wherein each of the first and second arms has a maximum outer diameter of less than 1 mm.

4. The surgical instrument assembly of claim 2, wherein each of the first arm and the second arm includes a shoulder joint, an elbow joint spaced distally from the shoulder joint, a wrist joint spaced distally from the shoulder joint and the elbow joint, and an effector joint spaced distally from the should, elbow, and wrist joints.

5. The surgical instrument assembly of claim 4, wherein each of the shoulder, elbow, wrist, and effector joints are controllable with a total of six wires within each of the first arm and the second arm.

6. The surgical instrument assembly of claim 4, wherein the shoulder joint, the elbow joint, the wrist joint, and the effector joint of the first arm are each independently controllable at the first control assembly housing.

7. The surgical instrument assembly of claim 1, wherein the first end effector is adjustable between the open configuration and the grasping configuration without manipulation of a wire connected with the first end effector.

8. The surgical instrument assembly of claim 1, wherein the first end effector is adjustable between the open configuration and the grasping configuration by relative longitudinal movement between the first end effector and the first arm.

9. The surgical instrument assembly of claim 1, comprising a vacuum source in fluid communication with one or more hollow channels of the first end effector.

10. The surgical instrument assembly of claim 1, wherein the first arm comprises a memory shape such that the first arm exhibits a predefined curvature when extended from the working channel.

11. The surgical instrument assembly of claim 1, wherein the first arm comprises a memory shaped wire, the memory shaped wire having a curved profile in a rested state and a straight profile when electrified.

12. The surgical instrument assembly of claim 1, wherein the first arm comprises a pressurized lumen, a curvature of the arm adjustable by varying the pressure of the lumen.

13. The surgical instrument assembly of claim 1, wherein the control assembly comprises a connector positioned at a distal of the control assembly to removably attach with a proximal end of the working channel having the diameter of 2 mm or less such that the first and second arms extend distally from the distal end of the control assembly and through an interior of the working channel having the diameter of 2 mm or less.

14. The surgical instrument assembly of claim 1, further comprising an articulating imaging source that includes: an articulation arm extending to a target area proximate to the first and second end effectors, and an imaging source attached to a distal end of the articulating arm, wherein all of the first arm, the second arm, and the articulating arm are configured to pass through the working channel having a diameter of 2 mm or less.

15. The surgical instrument assembly of claim 1, wherein the first end effector includes said jaws for grasping and a blade for cutting that is movable relative to said jaws.

16. A surgical instrument assembly, comprising:
   a first arm having a proximal end and a distal end, a first end effector located at the distal end of the first arm;
   a second arm having a proximal end and a distal end, a second end effector located at the distal end of the second arm; and
   a control assembly located at the proximal ends of the first and second arms, the control assembly including a first end effector input that actuates the first end effector, a second end effector input that actuates the second end effector, a first arm input that controls at least one degree of freedom of the first arm, and a second arm input that controls at least one degree of freedom of the second arm;

wherein the first and second arms are configured to pass through a working channel having a diameter of 2 mm or less while the first and second arms and first and second end effectors are manipulated by the control assembly, wherein the control assembly includes a first control assembly housing and a second control assembly housing that is separate from the first control assembly housing, the first control assembly housing comprising a first handle, the first arm input, and the first end effector input, and the second control assembly housing comprising a second handle, the second arm input, and the second end effector input, and wherein each of the first arm and the second arm includes a shoulder joint, an elbow joint spaced distally from the shoulder joint, a wrist joint spaced distally from the shoulder joint and the elbow joint, and an effector joint spaced distally from the should, elbow, and wrist joints.

17. The surgical instrument assembly of claim 16, wherein each of the shoulder, elbow, wrist, and effector joints are controllable with a total of six wires within each of the first arm and the second arm.

18. The surgical instrument assembly of claim 17, further comprising an articulating imaging source that includes: an articulation arm extending to a target area proximate to the first and second end effectors, and an imaging source attached to a distal end of the articulating arm, wherein all of the first arm, the second arm, and the articulating arm are configured to pass through the working channel having a diameter of 2 mm or less.

19. The surgical instrument assembly of claim 16, wherein the shoulder joint, the elbow joint, the wrist joint, and the effector joint of the first arm are each independently controllable at the first control assembly housing.

20. A surgical instrument assembly, comprising:
a first arm having a proximal end and a distal end, a first end effector located at the distal end of the first arm;
a second arm having a proximal end and a distal end, a second end effector located at the distal end of the second arm; and
a control assembly located at the proximal ends of the first and second arms, the control assembly including a first end effector input that actuates the first end effector, a second end effector input that actuates the second end effector, a first arm input that controls at least one degree of freedom of the first arm, and a second arm input that controls at least one degree of freedom of the second arm;
wherein the first and second arms are configured to pass through a working channel having a diameter of 2 mm or less while the first and second arms and first and second end effectors are manipulated by the control assembly, and wherein the control assembly comprises a connector positioned at a distal of the control assembly to removably attach with a proximal end of the working channel having the diameter of 2 mm or less such that the first and second arms extend distally from the distal end of the control assembly and through an interior of the working channel having the diameter of 2 mm or less.

21. The surgical instrument assembly of claim 20, further comprising an articulating imaging source that includes: an articulation arm extending to a target area proximate to the first and second end effectors, and an imaging source attached to a distal end of the articulating arm, wherein all of the first arm, the second arm, and the articulating arm are configured to pass through the working channel having a diameter of 2 mm or less.

22. The surgical instrument assembly of claim 20, wherein the first end effector includes jaws for grasping and a blade for cutting that is movable relative to said jaws.

23. A surgical instrument assembly, comprising:
a first arm having a proximal end and a distal end, a first end effector located at the distal end of the first arm, wherein at least the first end effector includes a pair of jaws for grasping and a blade for cutting that is movable relative to the pair of jaws;
a second arm having a proximal end and a distal end, a second end effector located at the distal end of the second arm; and
a control assembly located at the proximal ends of the first and second arms, the control assembly including a first end effector input that actuates the first end effector, a second end effector input that actuates the second end effector, a first arm input that controls at least one degree of freedom of the first arm, and a second arm input that controls at least one degree of freedom of the second arm;
wherein the first and second arms are configured to pass through a working channel having a diameter of 2 mm or less while the first and second arms and first and second end effectors are manipulated by the control assembly.

24. The surgical instrument assembly of claim 23, wherein the control assembly includes a first control assembly housing and a second control assembly housing that is separate from the first control assembly housing, the first control assembly housing comprising a first handle, the first arm input, and the first end effector input, and the second control assembly housing comprising a second handle, the second arm input, and the second end effector input.

25. The surgical instrument assembly of claim 24, wherein each of the first and second arms has a maximum outer diameter of less than 1 mm.

26. A method of operating a surgical instrument assembly, comprising:
advancing first and second arms through a working channel having a diameter of 2 mm or less, the first arm having a proximal end and a distal end, a first end effector located at the distal end of the first arm, and the second arm having a proximal end and a distal end, a second end effector located at the distal end of the second arm;
manipulating a first control assembly located at the proximal end of the first arm to actuate the first end effector between an open configuration and a closed configuration while the first and second arms are located through the working channel, the first end effector actuated by movement of a portion of the first end effector relative to the working channel;
manipulating a second control assembly located at the proximal end of the second arm to actuate the second end effector while the first and second arms are located through the working channel; and
after said advancing the first and second arms through the working channel having the diameter of 2 mm or less, removably attaching a proximal end of the working channel to a connector positioned at a distal end of the first and second control assemblies such that the first and second arms extend distally of the connector and through an interior of the working channel having the diameter of 2 mm or less.

27. The method of claim 26, wherein each of the first and second arms has a maximum outer diameter of less than 1 mm.

28. The method of claim 26, wherein the first end effector comprises jaws adjustable between the open configuration and the closed configuration.

29. The method of claim 28, wherein the first end effector is adjustable between the open configuration and the closed configuration without manipulation of a wire connected with the first end effector.

30. The method of claim 28, wherein the first end effector is adjustable between the open configuration and the closed configuration by relative longitudinal movement between the first end effector and the first arm.

31. The method of claim 26, further comprising applying a vacuum source to one or more hollow channels of the first end effector.

32. The method of claim 26, further comprising extending the first arm distally from the working channel such that a shape memory element of the first arm exhibits a predefined curvature along a portion of the first arm extending from the working channel.

* * * * *